United States Patent
Tomimori et al.

(10) Patent No.: US 9,000,931 B2
(45) Date of Patent: Apr. 7, 2015

(54) NOISE PROCESSING APPARATUS

(75) Inventors: Hideki Tomimori, Kawasaki (JP); Ken Sasaki, Tokyo (JP); Yasuhiko Nakano, Kawasaki (JP); Satoshi Sano, Kawasaki (JP); Yoshio Ishida, Tokyo (JP)

(73) Assignees: Fujitsu Limited, Kawasaki (JP); The University of Tokyo, Tokyo (JP)

( * ) Notice: Subject to any disclaimer, the term of this patent is extended or adjusted under 35 U.S.C. 154(b) by 340 days.

(21) Appl. No.: 13/483,350

(22) Filed: May 30, 2012

(65) Prior Publication Data
US 2013/0022209 A1    Jan. 24, 2013

Related U.S. Application Data

(63) Continuation of application No. PCT/JP2009/070137, filed on Nov. 30, 2009.

(51) Int. Cl.
*G08B 23/00* (2006.01)
*A61B 5/0245* (2006.01)
(Continued)

(52) U.S. Cl.
CPC .......... *A61B 5/0245* (2013.01); *A61B 5/18* (2013.01); *A61B 5/6893* (2013.01); *A61B 5/7214* (2013.01)

(58) Field of Classification Search
CPC .. A61B 5/18; A61B 5/0245; A61B 5/040861; G08B 21/06; B60W 2540/22
USPC .......... 600/372, 374, 393, 509, 547; 340/575, 340/576, 573.1, 500, 540; 180/272; 381/71.2, 71.4, 71.9, 94.1, 94.7, 86, 381/56, 58
See application file for complete search history.

(56) References Cited

U.S. PATENT DOCUMENTS 4,170,227 A    10/1979  Feldman et al.
5,002,063 A *   3/1991  Haner .................... 600/509
(Continued)

FOREIGN PATENT DOCUMENTS

| JP | 2003-235823 | 8/2003 |
| JP | 2006-198403 | 8/2006 |
| JP | 2009-142576 | 7/2009 |

OTHER PUBLICATIONS

Extended European Search Report, dated Sep. 2, 2013, in corresponding European Application No. 09851683.4 (6 pp.).

(Continued)

*Primary Examiner* — Xu Mei
*Assistant Examiner* — Jason R Kurr
(74) *Attorney, Agent, or Firm* — Staas & Halsey LLP

(57) ABSTRACT

A noise processing apparatus measures a first potential difference signal, between a first electrode and a second electrode that is used as a reference electrode, and measures a second potential difference signal, between the second electrode and a third electrode that is arranged on the steering unit in the apparatus. The apparatus calculates the difference between the intensities of the first potential difference signal and the second potential difference signal calculated at the predetermined intervals. The apparatus corrects the first potential difference signal or the second potential difference signal by using the calculated difference such that the intensities of the first potential difference signal and the second potential difference signal are canceled out. The apparatus calculates a differential signal indicating the difference between the first potential difference signal and the second potential difference signal by using the corrected potential difference signal, and outputs the differential signal.

15 Claims, 27 Drawing Sheets

(51) Int. Cl.
*A61B 5/18* (2006.01)
*A61B 5/00* (2006.01)

(56) References Cited

U.S. PATENT DOCUMENTS

| | | | | |
|---|---|---|---|---|
| 5,615,687 | A * | 4/1997 | Pritchard | 600/509 |
| 6,239,707 | B1 * | 5/2001 | Park | 340/576 |
| 7,894,887 | B2 * | 2/2011 | Yanai et al. | 600/509 |
| 8,847,769 | B2 * | 9/2014 | Ershov et al. | 340/575 |
| 2008/0069375 | A1 | 3/2008 | Lange | |
| 2009/0292216 | A1 | 11/2009 | Krch, Sr. et al. | |
| 2010/0049068 | A1 * | 2/2010 | Fuwamoto et al. | 600/509 |

OTHER PUBLICATIONS

International Search Report of Corresponding PCT Application PCT/JP2009/070137 mailed Feb. 23, 2010.

Tommimori et al, ECG measurement using Contact Electrode and Capacitive Electrode, 2008, pp. 717-718 with English Abstract.

* cited by examiner

FIG.8
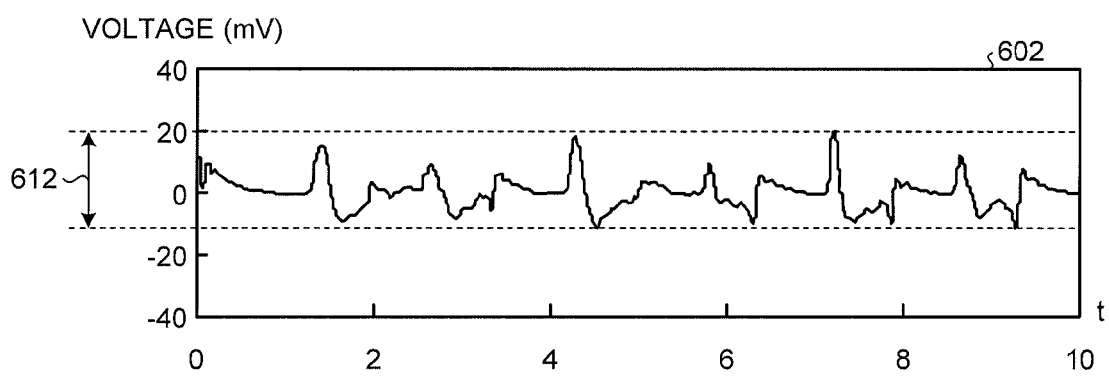
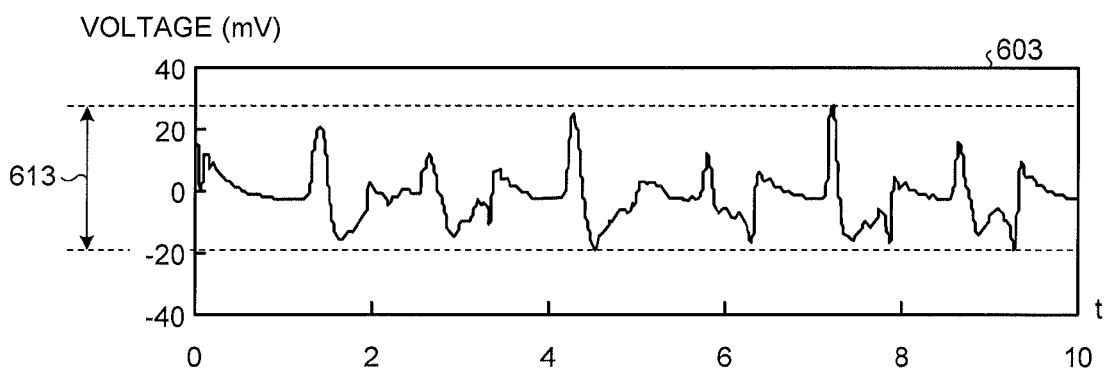

FIG.9B
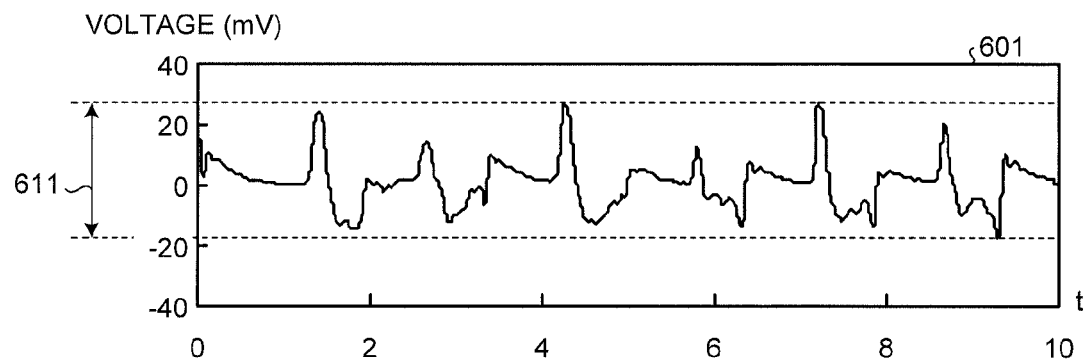
+ (POSITIVE)
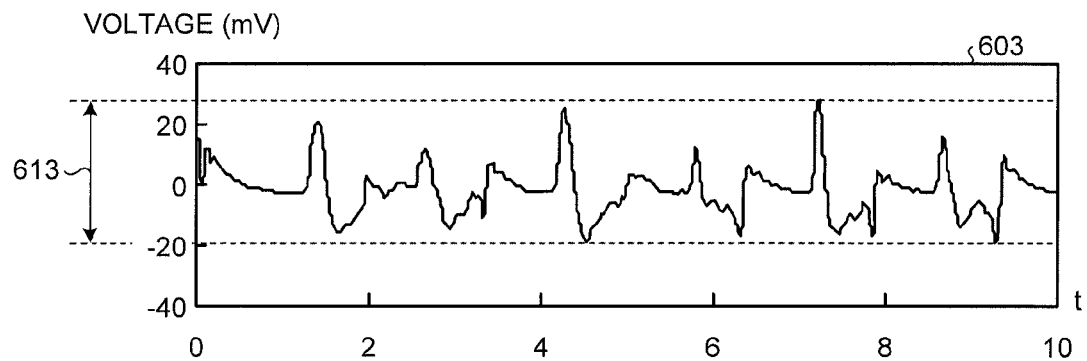
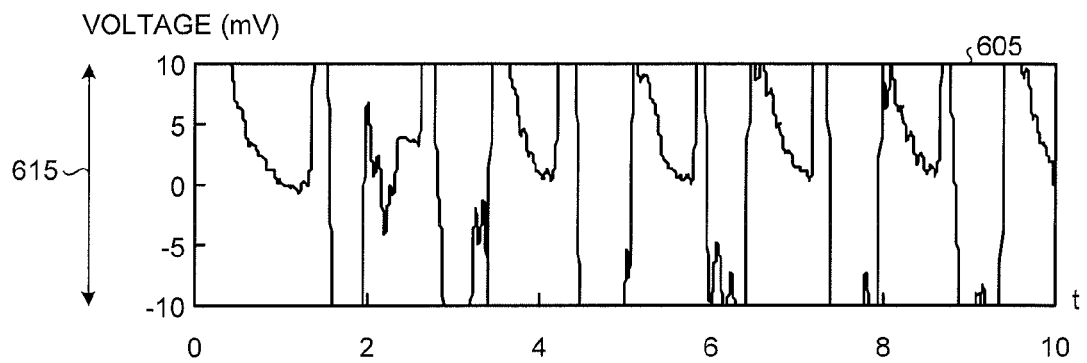

NOISE PROCESSING APPARATUS

CROSS-REFERENCE TO RELATED APPLICATION

This application is a continuation of International Application No. PCT/JP2009/070137, filed on Nov. 30, 2009, the entire contents of which are incorporated herein by reference.

FIELD

The embodiments discussed herein are directed to a noise processing apparatus and a noise processing program.

BACKGROUND

There is a detecting unit that detects the physical state of a subject by using the state of a subject's pulse or heartbeat. For example, the detecting unit arranged in a vehicle detects the physical state of a driver and thus reduces the occurrence of accidents caused by deterioration of the physical state of the driver.

For example, the detecting unit measures a potential difference signal between two electrodes that are brought into close contact with a subject and identifies, from the measured potential difference signal, an electrocardiographic signal that indicates the subject's pulse or heartbeat. Then, the detecting unit detects drowsiness or the degree of wakefulness as the subject's physical state by using the identified electrocardiographic signal.

For example, the electrodes that are brought into contact with the subject are arranged on, for example, a steering unit (steering wheel) or a seat surface in a vehicle. The electrodes arranged on the seat surface are brought into contact with the buttocks of the subject when the subject sits on the seat. The electrodes arranged at the steering wheel are brought into contact with the hands of the subject when the subject holds the steering wheel.

There is a processing unit that performs a reduction process for reducing noise contained in a potential difference signal. A vehicle in which the processing unit is arranged includes an electrode that is used as the reference electric potential, an electrode arranged on the steering unit, and an electrode arranged on a seat surface. The processing unit measures a potential difference signal between the electrode that is used as the reference electric potential and the electrode arranged on the steering unit and measures a potential difference signal between the electrode that is used as the reference electric potential and the electrode arranged on the seat surface. Then, the processing unit calculates the difference between the two potential difference signals to reduce the noise contained in the potential difference signal.

Furthermore, there is an apparatus that calculates heartbeat intervals for each heartbeat and then calculates the square mean value (root mean square of successive difference) of a standard deviation or a serial difference of the heartbeat intervals to remove irregular heartbeat intervals from the calculated heartbeat intervals.

Patent Literature 1: Japanese Laid-open Patent Publication No. 2009-142576

Patent Literature 2: Japanese Laid-open Patent Publication No. 2006-198403

SUMMARY

According to an aspect of an embodiment of the invention, a noise processing apparatus includes a first measuring unit that measures a first potential difference signal between a first electrode that is arranged at a location other than a steering unit in an apparatus and a second electrode that is used as a reference electrode. The noise processing apparatus includes a second measuring unit that measures a second potential difference signal between the second electrode and a third electrode that is arranged on the steering unit in the apparatus. The noise processing apparatus includes an intensity calculating unit that calculates, at predetermined intervals, an intensity of the first potential difference signal measured by the first measuring unit and an intensity of the second potential difference signal measured by the second measuring unit. The noise processing apparatus includes a difference calculating unit that calculates a difference between the intensity of the first potential difference signal and the intensity of the second potential difference signal, which are calculated by the intensity calculating unit at the predetermined intervals. The noise processing apparatus includes a correction unit that corrects, at the predetermined intervals, the first potential difference signal and/or the second potential difference signal by using the difference calculated by the difference calculating unit such that the difference between the intensity of the first potential difference signal and the intensity of the second potential difference signal are cancelled out. The noise processing apparatus includes a differential signal calculating unit that calculates, by using the potential difference signal corrected by the correction unit at the predetermined intervals, a differential signal indicating a difference between the first potential difference signal and the second potential difference signal. The noise processing apparatus includes an output processing unit that outputs the differential signal calculated by the differential signal calculating unit.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

BRIEF DESCRIPTION OF DRAWINGS

FIG. 8 is a schematic diagram illustrating the correction performed by a differential signal calculating unit according to the second embodiment;

FIG. 9B is a schematic diagram illustrating an addition process performed by the differential signal calculating unit according to the second embodiment;

DESCRIPTION OF EMBODIMENTS

As described previously, there is a processing unit that performs a reduction process for reducing noise. However, with the processing unit described above, there is a problem in that the noise contained in the potential difference signal is not appropriately reduced. Specifically, if a subject moves his/her body or an apparatus vibrates, the noise reduction is small compared with a case in which the subject does not move his/her body or the apparatus does not vibrate.

Preferred embodiments of a noise processing apparatus and a noise processing program disclosed in the present invention will be described in detail below with reference to the accompanying drawings. The present invention is not limited to the embodiments. Furthermore, the embodiments can be appropriately used in combination as long as processes do not conflict with each other.

[a] First Embodiment

Figure 1:
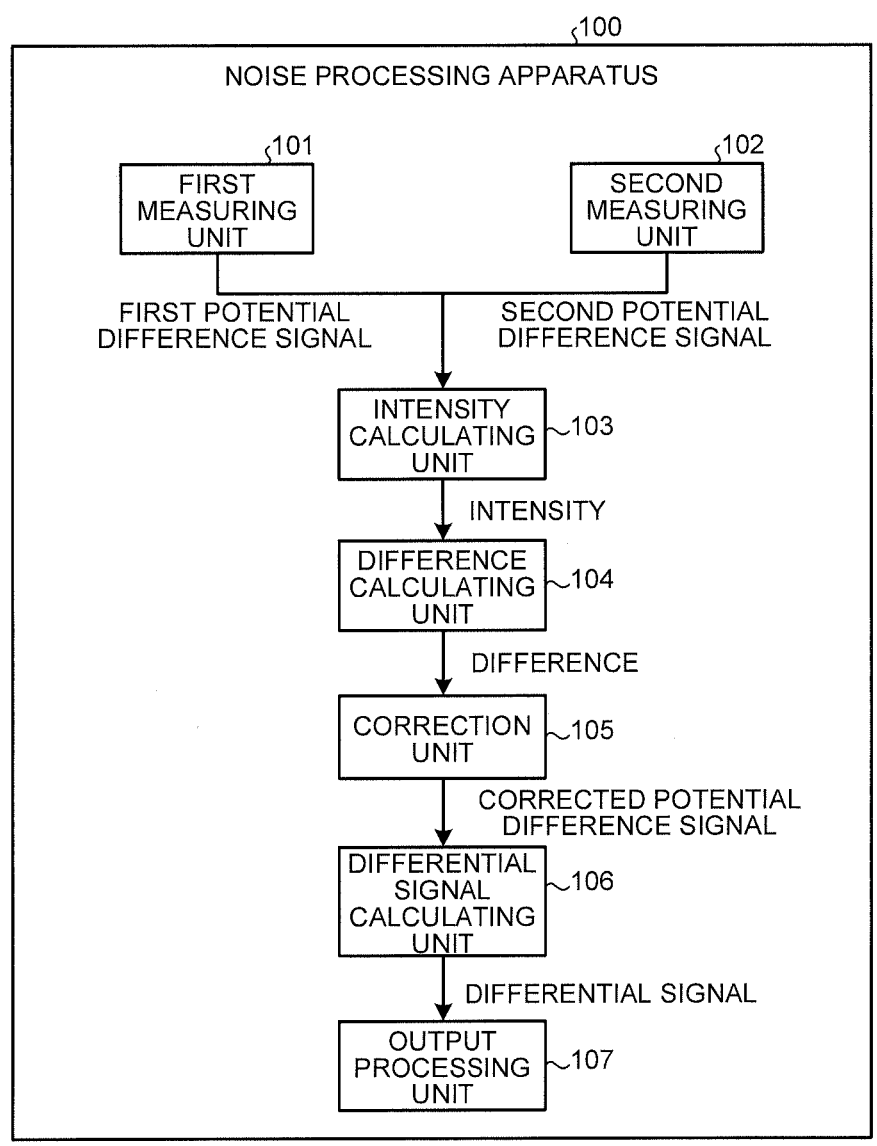
FIG. 1 is a block diagram illustrating an example configuration of a noise processing apparatus according to a first embodiment.

An example configuration of a noise processing apparatus 100 according to a first embodiment will be described here with reference to FIG. 1. FIG. 1 is a block diagram illustrating an example configuration of a noise processing apparatus according to a first embodiment. In the example illustrated in FIG. 1, the noise processing apparatus 100 includes a first measuring unit 101, a second measuring unit 102, an intensity calculating unit 103, a difference calculating unit 104, a correction unit 105, a differential signal calculating unit 106, and an output processing unit 107.

The first measuring unit 101 measures a first potential difference signal between a first electrode that is arranged in an apparatus at a location different from a steering unit and a second electrode that is used as the reference electrode. The second measuring unit 102 measures a second potential difference signal between a third electrode arranged on the steering unit of the apparatus and the second electrode any location may be used for arranging the first electrode as long as the location is opposite the steering unit across the heart of an operator using the steering unit and is electrically brought into contact with the operator. An example of the location includes a seat surface on which the operator that uses the steering unit is sitting.

The intensity calculating unit 103 calculates, at predetermined intervals, the intensity of the first potential difference signal measured by the first measuring unit 101 and the intensity of the second potential difference signal measured by the second measuring unit 102. Then, the difference calculating unit 104 calculates the difference between the intensity of the first potential difference signal and the intensity of the second potential difference signal that are calculated by the intensity calculating unit 103 at the predetermined intervals.

Then, the correction unit 105 corrects the first potential difference signal or the second potential difference signal at the predetermined intervals by using the difference calculated by the difference calculating unit 104 in the direction in which the difference between the intensity of the first potential difference signal and the intensity of the second potential difference signal is canceled. Then, by using a potential difference signal that is corrected by the correction unit 105 at the predetermined intervals, the differential signal calculating unit 106 calculates a differential signal that indicates the difference between the first potential difference signal and the second potential difference signal. Then, the output processing unit 107 outputs the differential signal calculated by the differential signal calculating unit 106. The differential signal that is output by the output processing unit 107 is a potential difference signal that indicates the potential difference between the first electrode and the third electrode and becomes a potential difference signal between the electrodes that are brought into contact with two locations separated by the heart. The differential signal is also referred to as a potential difference signal.

As described above, according to the first embodiment, after correcting the intensity of the electric potential signals measured for each electrode, the differential signal is calculated, in the state in which electrodes are brought into contact with a subject at two locations separated by the heart. Therefore, according to the first embodiment, noise can be appropriately reduced from the potential difference signal between the electrodes that are brought into contact with two locations separated by the heart. Specifically, even if a subject moves his/her body or an apparatus vibrates, noise can also be reduced by an amount similar to a case in which the subject does not move his/her body or the apparatus does not vibrate.

If a subject moves his/her body or an apparatus vibrates, the noise reduction is small compared with a case in which the subject does not move his/her body or the apparatus does not vibrate. In the following, the reason for this will be examined. If noise is reduced by calculating the difference between two potential difference signals, the noise intensities contained in potential difference signals are not the same unless the intensities of the two potential difference signals are the same, and thus the noise is not appropriately reduced even if the difference between the two potential difference signals is calculated. However, for example, there is a method for adjusting the intensities of the two potential difference signals by adjusting the area of an electrode.

The intensity of a potential difference signal changes depending on the impedance of the electrode itself or the impedance of a contact portion between an electrode and a subject. As the impedance increases, noise contained in the potential difference signal becomes strong and is added to the potential difference signal generated from a heartbeat; therefore, the intensity of the potential difference signal also becomes strong. The impedance of the contact portion changes depending on the contact state between an electrode and a subject. If a subject moves his/her body or an apparatus vibrates, it is assumed that the contact state between an electrode arranged on the seat surface and the subject easily changes compared with the contact state between an electrode arranged on the steering unit and the subject.

Specifically, it is assumed that the contact state between the electrode arranged on the seat surface and the subject easily changes compared with the contact state between the electrode arranged on the steering unit and the subject, and it is assumed that the impedance of the electrode arranged on the seat surface easily changes compared with the impedance of the electrode arranged on the steering unit. Furthermore, it is assumed that the noise intensities contained in each of the potential difference signals differ unless the potential difference signal from the electrode arranged on the seat surface and the potential difference signal of the electrode arranged on the steering unit change in a similar manner. Accordingly, it is assumed that, even if the difference between the two potential difference signals is calculated, the noise contained in the differential signal is not adequately canceled, and thus noise is not reduced.

In light of the circumstances described above, according to the first embodiment, because the difference is calculated after correcting the intensities of two potential difference signals such that the intensities thereof becomes the same, the noise contained in the differential signal can appropriately be reduced. In other words, according to the first embodiment, even if the two potential difference signals change in a different manner, it is still possible to appropriately reduce the noise.

[b] Second Embodiment

Configuration of the Noise Processing Apparatus

Figure 2:
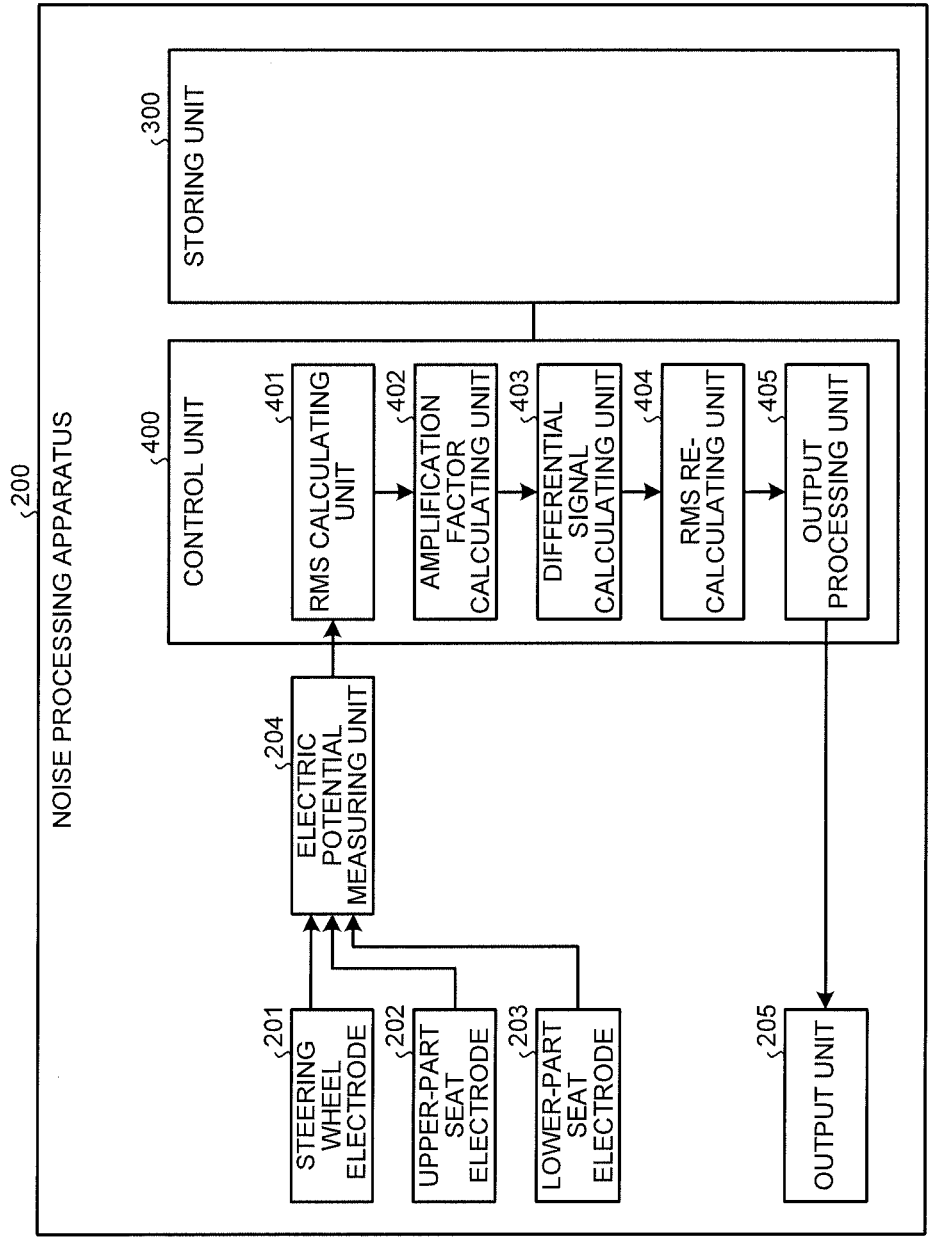
FIG. 2 is a block diagram illustrating an example configuration of a noise processing apparatus according to a second embodiment.

In the following, a noise processing apparatus 200 according to a second embodiment will be described. An example configuration of the noise processing apparatus 200 according to the second embodiment will be described with reference to FIG. 2. FIG. 2 is a block diagram illustrating the configuration of a noise processing apparatus according to a second embodiment. In the example illustrated in FIG. 2, the noise processing apparatus 200 includes a steering wheel electrode 201, an upper-part seat electrode 202, a lower-part seat electrode 203, an electric potential measuring unit 204, an output unit 205, a storing unit 300, and a control unit 400.

Electrode

In the following, a case will be described in which the steering wheel electrode 201 is arranged at a steering wheel in a vehicle as a second electrode, and the upper-part seat electrode 202 and the lower-part seat electrode 203 are on a seat surface in the vehicle as a first electrode and a third electrode, respectively, unless otherwise stated. Furthermore, a target person for whom an electric potential is measured is referred to as a subject. However, the present invention is not limited thereto as long as both the steering wheel electrode 201 and the upper-part seat electrode 202 are arranged at a location in which they are brought into electrical contact with the subject in the time period for which an electric potential is measured. For example, if an electric potential related to an electrocardiographic wave is measured while the subject operates an apparatus, it is assumed that the steering wheel electrode 201 and the upper-part seat electrode 202 are arranged at locations in which they are naturally brought into electrical contact with the subject via his/her motion during the operation. If the steering wheel electrode 201 and the upper-part seat electrode 202 are arranged at such a location, the subject does not need to deliberately make an effort to measure his/her electrical potential.

Furthermore, both the steering wheel electrode 201 and the upper-part seat electrode 202 are arranged at two locations as long as they are separated by the heart of the subject. For example, both the steering wheel electrode 201 and the upper-part seat electrode 202 may also be arranged on a steering wheel and a backrest of a seat in a vehicle or they may also be arranged in any combination of locations. Furthermore, both the upper-part seat electrode 202 and the lower-part seat electrode 203 may also be arranged on either one of the two locations opposite the subject with the heart of the subject located therebetween. For example, both the upper-part seat electrode 202 and the lower-part seat electrode 203 may also be arranged on the backrest of the seat or may also be arranged on an arbitrary location. If an electric potential is measured when the subject stands, both the upper-part seat electrode 202 and the lower-part seat electrode 203 may be arranged at the location that, for example, the subject steps on.

Figure 3:
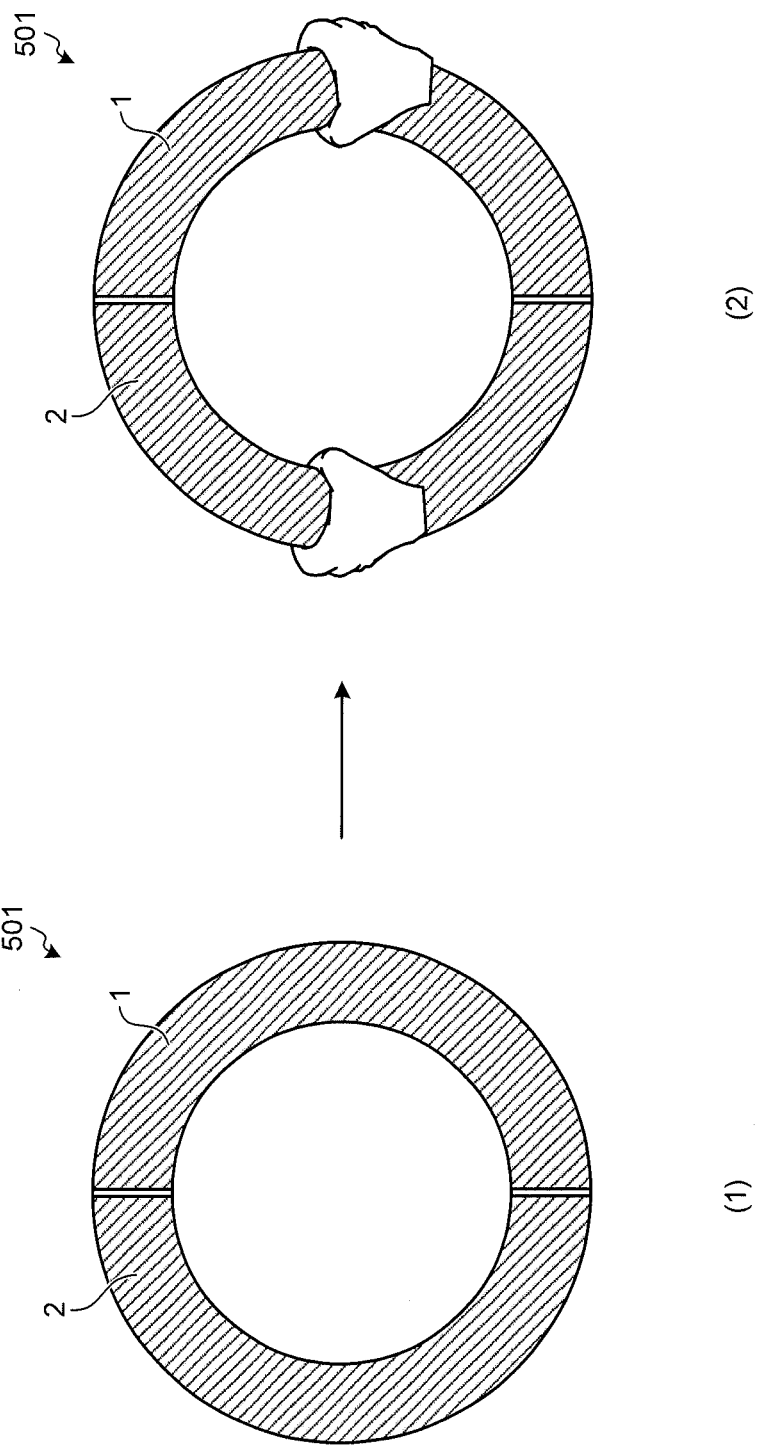
FIG. 3 is a schematic diagram illustrating an example of steering wheel electrodes according to the second embodiment.

The steering wheel electrode 201 is connected to the electric potential measuring unit 204. Furthermore, the steering wheel is also referred to as a steering unit or a steering wheel. An example structure of the steering wheel electrode 201 will be described here with reference to FIG. 3. FIG. 3 is a schematic diagram illustrating an example of steering wheel electrodes according to the second embodiment. Reference numeral 501 illustrated in FIG. 3 denotes a steering wheel. Reference numerals "1" and "2" illustrated in FIG. 3 denote steering wheel electrodes 201. In the example illustrated in (1) of FIG. 3, the two steering wheel electrodes 201 with a uniform size are arranged in the circumferential direction of the steering wheel 501. In the following, each of the two steering wheel electrodes 201 are represented by a steering wheel electrode "1" and a steering wheel electrode "2".

In the following, a case will be described in which two steering wheel electrodes 201 are arranged on the steering wheel 501 unless otherwise stated. However, the present invention is not limited thereto. For example, a single steering wheel electrode, three or more steering wheel electrodes, or any number of steering wheel electrodes may also be arranged on the steering wheel 501.

The steering wheel electrodes 201 are brought into electrical contact with the subject when the subject holds the steering wheel 501. In the example illustrated in (2) of FIG. 3, the steering wheel electrode "1" is brought into contact with the right hand of the subject and the steering wheel electrode "2" is brought into contact with the left hand of the subject.

In the following, the upper-part seat electrode 202 and the lower-part seat electrode 203 will be described. Both the upper-part seat electrode 202 and the lower-part seat electrode 203 are brought into contact with the electric potential measuring unit 204. The upper-part seat electrode 202 is arranged at a location other than the location of the electrode that is arranged on the steering wheel 501. For example, both the upper-part seat electrode 202 and the lower-part seat electrode 203 are arranged on seat 502 in the vehicle. The lower-part seat electrode 203 is grounded to the vehicle and becomes equal to the electric potential of the vehicle. The lower-part seat electrode 203 is used as the reference electrode by the noise processing apparatus 100.

Figure 4:
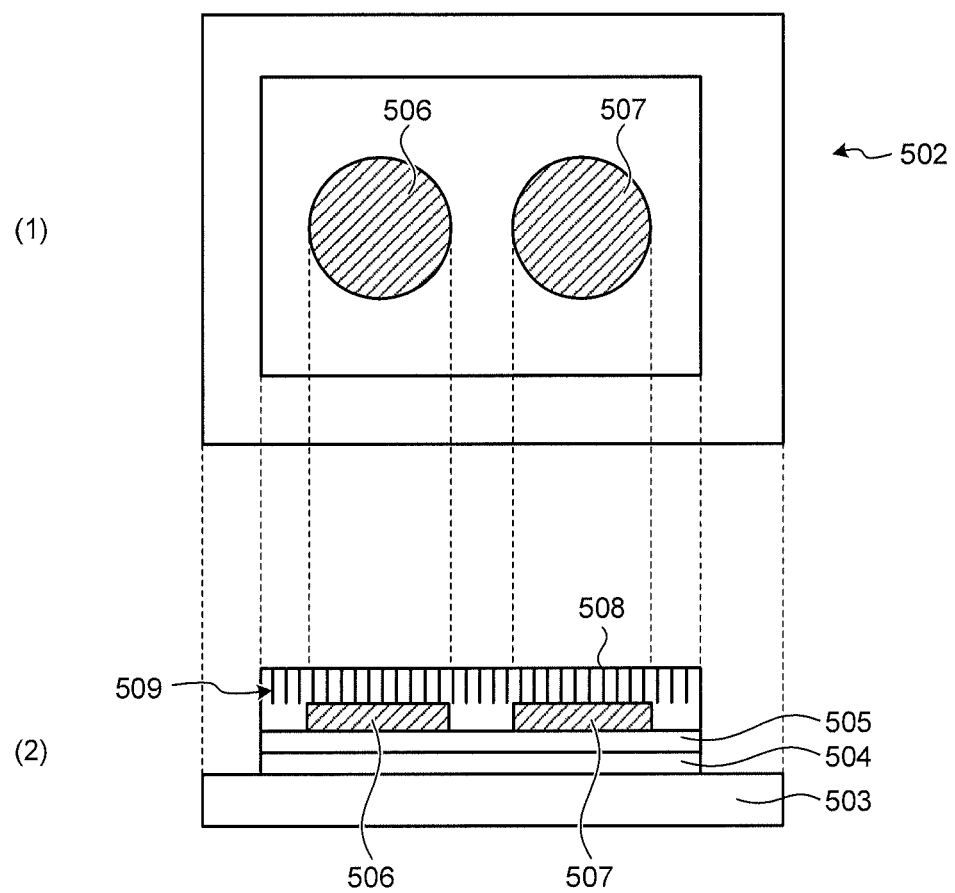
FIG. 4 is a schematic diagram illustrating an example of a lower-part seat electrode and an upper-part seat electrode arranged on a vehicle seat.

An example of the upper-part seat electrode 202 and the lower-part seat electrode 203 arranged on the seat 502 in the vehicle will be described here with reference to FIG. 4. FIG. 4 is a schematic diagram illustrating an example of a lower-part seat electrode and an upper-part seat electrode arranged on a vehicle seat. The symbol (1) in FIG. 4 illustrates the seat in the vehicle viewed from the top. The symbol (2) FIG. 4 is a sectional view of the seat in the vehicle. In FIG. 4, reference numeral 502 denotes a vehicle seat, reference numeral 503 denotes a seat member that is a member of the seat 502, reference numeral 504 denotes the lower-part seat electrode 203, reference numeral 505 denotes an insulator, and reference numerals 506 and 507 each denotes the upper-part seat electrode 202. Furthermore, in FIG. 4, reference numeral 508 denotes a protection member and reference numeral 509 denotes a conductive part.

In the example illustrated in FIG. 4, the lower-part seat electrode 504, the insulator 505, the upper-part seat electrodes 506 and 507, and the protection member 508 are sequentially stacked on the seat member 503. Furthermore, the conductive part 509 is arranged on the protection member 508. The conductive part 509 is connected to the upper-part seat electrodes 506 and 507. For example, the protection member 508 has an opening and the conductive part 509 is arranged on the inner wall of the opening. In the example illustrated in FIG. 4, as illustrated by reference numerals 506 and 507 in FIG. 4, the upper-part seat electrodes 506 and 507 are separated into two. In such a case, the upper-part seat electrodes 506 and 507 correspond to the right side and the left side of the buttocks of the subject, respectively. The lower-part seat electrode 504 faces the upper-part seat electrodes 506 and 507 via the insulator 505. In this case, the upper-part seat electrodes 202 are separated into two; however, they may not be separated.

In the following, a case will be described in which the two separated upper-part seat electrodes 506 and 507 are not distinguished; however, the present invention is not limited thereto. For example, the two separated upper-part seat electrodes 506 and 507 may also be electrically independent of each other and the electric potential measuring unit 204, which will be described later, may also separately measure the electric potential of each of the upper-part seat electrodes 506 and 507.

This section refers back to FIG. 2. The upper-part seat electrode 202 is brought into electrical contact with the subject when the subject sits on the seat 502. In the example illustrated in FIG. 4, the subject sits on the seat 502 and thus the upper-part seat electrode 202 is brought into contact with the buttocks of the subject via the conductive part 509. Furthermore, in the second embodiment, a case will be described, as an example, in which the upper-part seat electrode 202 is brought into contact with the subject unless otherwise stated. Specifically, in the second embodiment, a case will be described, as an example, in which the subject sits on the seat 502.

Electric Potential Measuring Unit

The electric potential measuring unit 204 is connected to the steering wheel electrode 201, the upper-part seat electrode 202, the lower-part seat electrode 203, and the control unit 400. An example of the electric potential measuring unit 204 includes an operational amplifier. The electric potential measuring unit 204 measures the electric potential of two locations separated by the heart of the subject. Specifically, the electric potential measuring unit 204 measures the electric potential of the steering wheel electrode 201 or the upper-part seat electrode 202 obtained when the electric potential of the vehicle is used as the reference electric potential. Specifically, the electric potential measuring unit 204 measures the electric potential of the subject's hands by measuring the electric potential of the steering wheel electrode "1" and the steering wheel electrode "2", whereas it measures the electric potential of the subject's buttocks by measuring the electric potential of the upper-part seat electrode 202.

More specifically, the electric potential measuring unit 204 measures the potential difference between the lower-part seat electrode 203 that is used as the reference electric potential and the upper-part seat electrode 202 and takes this measured potential difference to be the electric potential of the upper-part seat electrode 202. Furthermore, the electric potential measuring unit 204 measures the potential difference between the lower-part seat electrode 203 that is used as the reference electric potential and the steering wheel electrode 201 and takes this measured potential difference to be the electric potential of the steering wheel electrode 201.

In the following, each of the values of the potential difference successively measured from a certain time is referred to as a potential difference signal instead of limiting a value of the potential difference obtained at a certain time. Furthermore, a potential difference signal related to the upper-part seat electrode 202 measured by the electric potential measuring unit 204 is referred to as a first potential difference signal. Furthermore, a potential difference signal related to the steering wheel electrode 201 measured by the electric potential measuring unit 204 is referred to as a second potential difference signal.

Figure 5:
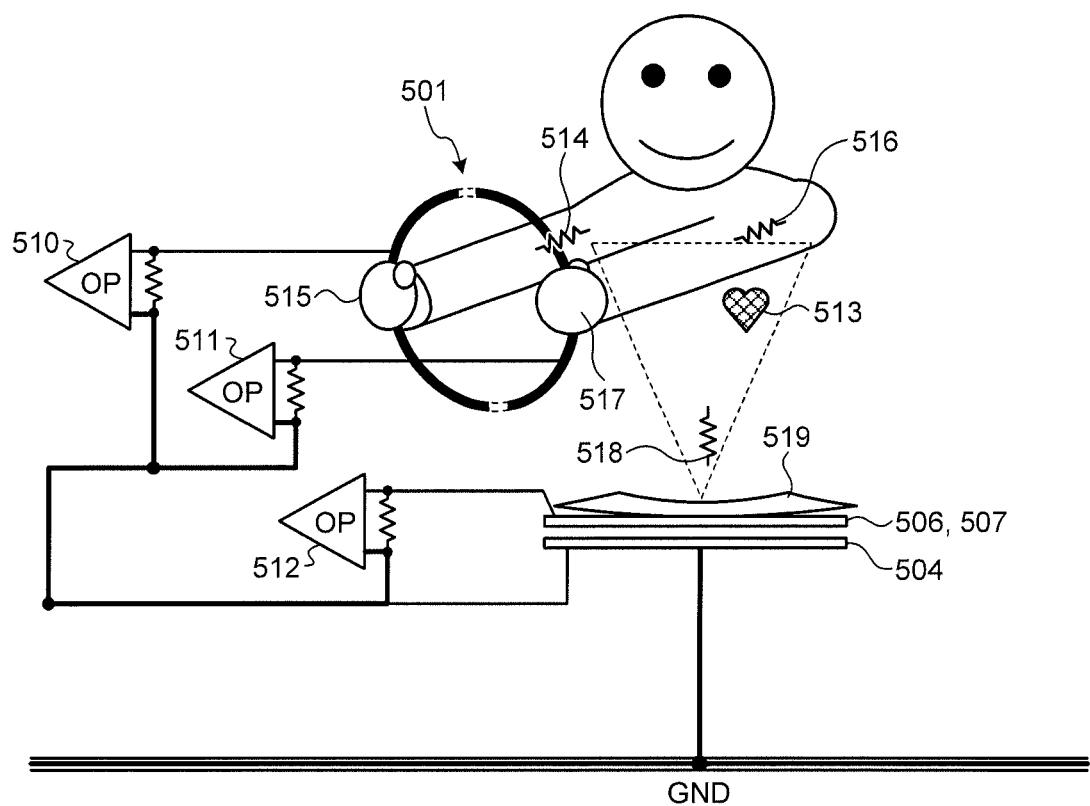
FIG. 5 is a schematic diagram illustrating an electric potential measured by an electric potential measuring unit according to the second embodiment.

The electric potentials measured by the electric potential measuring unit 204 will be further described with reference to FIG. 5. FIG. 5 is a schematic diagram illustrating an electric potential measured by an electric potential measuring unit according to the second embodiment. In FIG. 5, for convenience of description, a description will be given of a case using an example in which one of the two steering wheel electrodes 201 is brought into contact with the left hand of the subject and the other of the two steering wheel electrodes 201 is brought into contact with the right of the subject.

The portion from the heart to the arms of the subject can be assumed to be an electrical resistance component. The hands of the subject can be assumed to be an electrical resistor capacitor (RC) parallel circuit. The portion from the heart to the buttocks of the subject can be assumed to be an electrical resistance component. Furthermore, clothes, such as trousers or a skirt, can be assumed to be an electrical RC parallel circuit. Accordingly, the schematic diagram illustrated in FIG. 5 is an equivalent circuit including the subject. In FIG. 5, reference numerals 510 to 512 denote an operational amplifier and correspond to the electric potential measuring unit 204. Reference numeral 513 denotes the heart of the subject. Reference numeral 514 denotes a resistance component corresponding to the portion from the heart 513 to the right arm of the subject. Reference numeral 515 denotes an RC parallel circuit corresponding to the right arm of the subject. Reference numeral 516 denotes a resistance component corresponding to the portion from the heart 513 to the left arm of the subject. Reference numeral 517 denotes an RC parallel circuit corresponding to the left hand of the subject. Reference numeral 518 denotes a resistance component corresponding to the portion from the heart 513 to the buttocks of the subject. Reference numeral 519 denotes an RC parallel circuit corresponding to the clothes that the subject is wearing.

As illustrated in FIG. 5, the operational amplifier 510 includes two inputs. In the operational amplifier 510, the cardiac action potential of the heart 513 is input from the steering wheel electrode "1" via the resistance 514 and the RC parallel circuit 515 with respect to one input, whereas the electric potential of the vehicle body corresponding to the reference electric potential is input from the lower-part seat electrode 203 with respect to the other input. Then, the operational amplifier 510 amplifies the cardiac action potential obtained when the electric potential of the frame of the vehicle body is used as the reference electric potential and outputs the cardiac action potential. Specifically, in the example illustrated in FIG. 5, the operational amplifier 510 detects the cardiac action potential from the right hand of the subject, amplifies the detected cardiac action potential, and outputs the amplified cardiac action potential.

Similarly to the operational amplifier 510, an operational amplifier 511 receives an input of the cardiac action potential of the heart 513 from the steering wheel electrode "2" via the resistance 516 and the RC parallel circuit 517, amplifies the cardiac action potential, and outputs it. Specifically, the operational amplifier 511 detects the cardiac action potential from the left hand of the subject, amplifies it, and outputs the amplified cardiac action potential.

Similarly to the operational amplifier 510, the operational amplifier 512 receives an input of the cardiac action potential of the heart 513 from the upper-part seat electrode 202 via the resistance 518 and the RC parallel circuit 519, amplifies the cardiac action potential, and outputs it. Specifically, the operational amplifier 512 detects the cardiac action potential from the buttocks of the subject, amplifies it, and outputs the amplified cardiac action potential.

The reason for outputting the cardiac action potential amplified by the operational amplifiers 510 to 512 is that the cardiac action potential obtained when the electric potential of the frame of the vehicle body is used as the reference electric potential is weak. The operational amplifiers 510 to 512 amplify the cardiac action potential using a fixed amplification factor. Because the cardiac action potential detected from the buttocks of the subject is detected via the RC parallel circuit 519, i.e., is detected via the clothes that the subject is wearing, the detected cardiac action potential is smaller than that detected from the hands of the subject. Specifically, the noise of the cardiac action potential detected from the buttocks of the subject is greater than that detected from the hands of the subject.

Figure 6A:
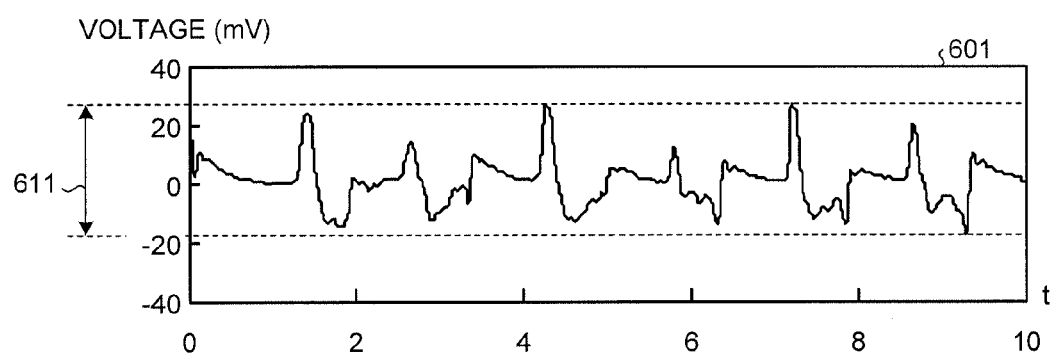
FIG. 6A is a schematic diagram illustrating an example of a first potential difference signal according to the second embodiment.
Figure 6B:
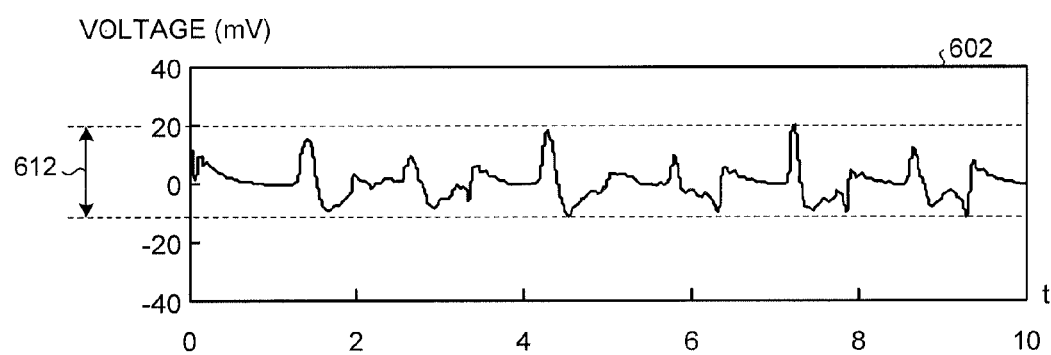
FIG. 6B is a schematic diagram illustrating an example of a second potential difference signal according to the second embodiment.

In the following, an example of the first potential difference signal and the second potential difference signal measured by the electric potential measuring unit 204 will be described with reference to FIGS. 6A and 6B. FIG. 6A is a schematic diagram illustrating an example of a first potential difference signal according to the second embodiment. FIG. 6B is a schematic diagram illustrating an example of a second potential difference signal according to the second embodiment. Reference numeral 601 denotes an example of the first potential difference signal. Reference numeral 602 denotes an example of the second potential difference signal. In reference numerals 601 and 602, the vertical axis indicates the value of the potential difference signal and the horizontal axis is the time axis. In the following, the time axis indicates the elapsed time after the start time of a process indicated by "0". Reference numeral 611 denotes the amplitude of the first potential difference signal and is about 40 mV in the example illustrated in FIG. 6A. Reference numeral 612 denotes the amplitude of the second potential difference signal and is about 25 mV in the example illustrated in FIG. 6B.

The output unit 205 is connected to the control unit 400. The output unit 205 receives information from the control unit 400 and outputs the received information. The information that is output by the output unit 205 will not be described in detail here but will be described later together with components related to each other.

Storing Unit

The storing unit 300 is connected to the control unit 400. The storing unit 300 stores therein data used for various processes performed by the control unit 400. The storing unit 300 is a semiconductor memory device, such as a random access memory (RAM), a read only memory (ROM), a flash memory, and the like or a storage device, such as a hard disk, an optical disk, and the like.

Control Unit

The control unit 400 is connected to the electric potential measuring unit 204, the output unit 205, and the storing unit 300. The control unit 400 has an internal memory for storing therein data and programs prescribing various kinds of procedures and controls various kinds of processes. The control unit 400 is an electronic circuit, such as an application specific integrated circuit (ASIC), a field programmable gate array (FPGA), a central processing unit (CPU), a micro processing unit (MPU), and the like. In the example illustrated in FIG. 2, the control unit 400 includes an RMS calculating unit 401, an amplification factor calculating unit 402, a differential signal calculating unit 403, an RMS re-calculating unit

404, and an output processing unit 405. The abbreviation RMS stands for "root mean square value".

For the first potential difference signal and the second potential difference signal measured by the electric potential measuring unit 204, the RMS calculating unit 401 calculates the intensity of each potential difference signal at predetermined intervals. The RMS calculating unit 401 is also referred to as an intensity calculating unit. For example, the RMS calculating unit 401 calculates, at 3-second intervals, the intensity of the potential difference signal by using a potential difference signal obtained between during the 3 seconds before the process time begins.

In the second embodiment, a description will be given of a case in which the RMS calculating unit 401 calculates the intensity of the potential difference signal at 3-second intervals; however, the present invention is not limited thereto. For example, the RMS calculating unit 401 may also calculate the intensity of the potential difference signal at 4-second intervals, at 2-second intervals, or at arbitrary intervals. Furthermore, for example, the RMS calculating unit 401 may also sequentially calculate the intensity of the potential difference signal in real time. Furthermore, in the second embodiment, a description will be given of a case in which the RMS calculating unit 401 calculates the intensity of a potential difference signal by using a potential difference signal during the 2 seconds before the process time begins; however, the present invention is not limited thereto. For example, the RMS calculating unit 401 may also calculates the intensity by using the potential difference signal during the 3 seconds before the process time begins or another time period before the process time begins.

Furthermore, for example, the RMS calculating unit 401 calculates the intensity of the potential difference signal by calculating the RMS of the potential difference signal. For example, the RMS calculating unit 401 calculates the RMS using "mathematical formula 1" or "mathematical formula 2".

mathematical formula 1

$$\sqrt{\frac{1}{T}\int_0^T i^2 \, dt} \quad (1)$$

mathematical formula 2

$$\sqrt{\frac{1}{T}\int_0^T (i - \bar{i})^2 \, dt} \quad (2)$$

A brief description of "mathematical formula 1" and "mathematical formula 2" will be given here. The formulas indicated by "mathematical formula 1" and "mathematical formula 2" are used to calculate the RMS between the time "0" and "T". The symbol "i" represented in "mathematical formula 1" and "mathematical formula 2" indicates the value of the potential difference signal. Specifically, in "mathematical formula 1", the average value of "i" squared between the time "0" and "T" is calculated and then the square root of the calculated average value is calculated.

Figure 7:
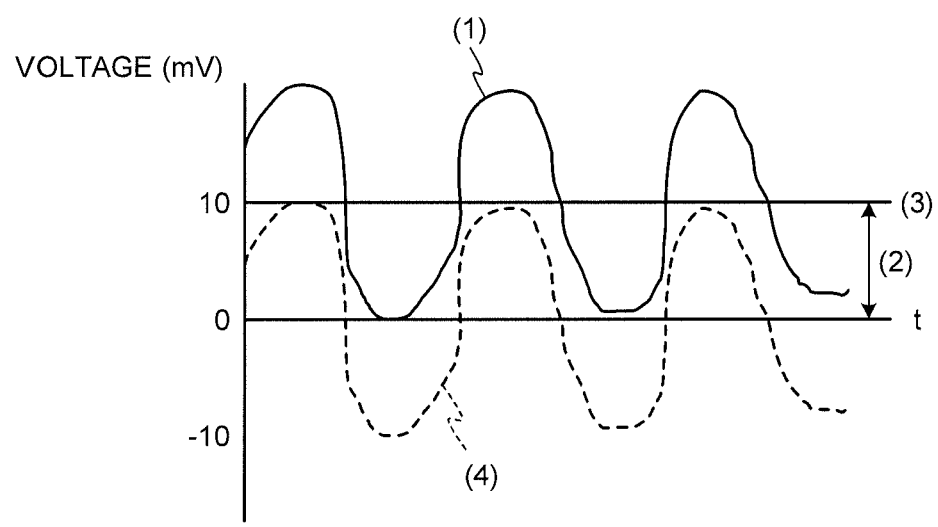
FIG. 7 is a schematic diagram illustrating mathematical formula 2 used to calculate an RMS.

A description of "mathematical formula 2" will be given with reference to FIG. 7. FIG. 7 is a schematic diagram illustrating mathematical formula 2, which is used to calculate an RMS. The symbol (1) in FIG. 7 illustrates an example of a potential difference signal measured by the electric potential measuring unit 204. The symbol (2) in FIG. 7 illustrates an offset applied to the potential difference signal measured by the electric potential measuring unit 204. The symbol (3) in FIG. 7 illustrates the average intensity of the potential difference signals measured by the electric potential measuring unit 204. The symbol (4) in FIG. 7 illustrates an example of a potential difference signal from which an offset is removed from the potential difference signal measured by the electric potential measuring unit 204.

As illustrated in (1) and (2) of FIG. 7, an offset is applied to the potential difference signal measured by the electric potential measuring unit 204. Accordingly, as illustrated in (4) of FIG. 7, the RMS calculating unit 401 may also calculate an RMS after removing the offset from the potential difference signal. Specifically, in "mathematical formula 2", the average value of the "values of subtracting the (average value of i) from i" squared between the time "0" and "T" is calculated and then the square root of the calculated average value is calculated. The (average value of i) corresponds to the average intensity of the potential difference signals illustrated in (4) of FIG. 7.

For example, if the RMS calculating unit 401 calculates the RMS of the first potential difference signals illustrated in FIG. 6A, a value of "1.49 mV" is obtained. Furthermore, if the RMS calculating unit 401 calculates the RMS of the second potential difference signals illustrated in FIG. 6B, a value of "1 mV" is obtained.

The amplification factor calculating unit 402 calculates the difference between the intensity of the first potential difference signal and the intensity of the second potential difference signal calculated by the RMS calculating unit 401 at predetermined intervals. Specifically, every time the RMS calculating unit 401 calculates the intensity of a potential difference signal, the amplification factor calculating unit 402 calculates the difference between the calculated intensity of the potential difference signal. Furthermore, the amplification factor calculating unit 402 is also referred to as a difference calculating unit. For example, the amplification factor calculating unit 402 divides the RMS "1.49 mV" related to the first potential difference signal by the RMS "1 mV" related to the second potential difference signal to calculate a difference of "1.49".

By using the difference calculated by the amplification factor calculating unit 402, the differential signal calculating unit 403 corrects, at predetermined intervals, the first potential difference signal and the second potential difference signal such that the intensities of the first potential difference signal and the second potential difference signal become equal. The differential signal calculating unit 403 is also referred to as a correction unit. For example, a description will be given of a case, as an example, in which the amplification factor calculating unit 402 calculates the difference by dividing the intensity of the first potential difference signal by the intensity of the second potential difference signal. In such a case, the differential signal calculating unit 403 corrects the second potential difference signal by using the difference "1.49" calculated by the amplification factor calculating unit 402. Specifically, the differential signal calculating unit 403 multiplies the second potential difference signal by "1.49" to determine the multiplication result of the potential difference signal to be the corrected second potential difference signal.

The correction performed by the differential signal calculating unit 403 according to the second embodiment will be described here with reference to FIG. 8. FIG. 8 is a schematic diagram illustrating the correction performed by a differential signal calculating unit according to the second embodiment. Reference numeral 603 denotes the corrected second potential difference signal. In reference numeral 603, the vertical axis indicates the value of the potential difference signal and the horizontal axis indicates the time axis. Reference numeral 613 denotes the amplitude of the corrected second potential difference signal and is about 40 mV in the example illustrated in FIG. 8.

As illustrated by reference numerals 602 and 603 in FIG. 8, the differential signal calculating unit 403 multiplies the second potential difference signal before correction by "1.49" and defines the multiplication result of the potential difference signal as the corrected second potential difference signal. Accordingly, as illustrated by reference numeral 612 in FIG. 8, in the second potential difference signal before the correction, the amplitude is about 25 mV, whereas, as illustrated by reference numeral 613 in FIG. 8, in the corrected second potential difference signal, the amplitude is about 40 mV. In the example illustrated in numeral number 611 in FIG. 6A, the amplitude of the first potential difference signal is about 40 mV. In other words, the intensity of the corrected second potential difference signal is the same as that of the first potential difference signal.

In the above description, a description has been given of a case in which the amplification factor calculating unit 402 calculates the difference by dividing the intensity of the first potential difference signal by the intensity of the second potential difference signal. Furthermore, a description has been given of a case in which the differential signal calculating unit 403 corrects the second potential difference signal by using the difference calculated by the amplification factor calculating unit 402. However, the present invention is not limited thereto. Any method may be used as long as, as a result of the correction performed by the differential signal calculating unit 403, the intensities of the first potential difference signal and the second potential difference signal become the same. For example, the amplification factor calculating unit 402 may calculate the difference by dividing the intensity of the second potential difference signal by the intensity of the first potential difference signal and the differential signal calculating unit 403 may correct the first potential difference signal by using the difference calculated by the amplification factor calculating unit 402. Similarly, the differential signal calculating unit 403 may also correct both the first potential difference signal and the second potential difference signal such that the intensities of the first potential difference signal and the second potential difference signal become the same.

Furthermore, by using the corrected potential difference signal, the differential signal calculating unit 403 calculates, at predetermined intervals, a differential signal indicating the difference between the first potential difference signal and the second potential difference signal. Specifically, the differential signal calculating unit 403 calculates the first differential signal by performing a subtraction process for subtracting the second potential difference signal from the first potential difference signal or performing a subtraction process for subtracting the first potential difference signal from the second potential difference signal. Furthermore, the differential signal calculating unit 403 calculates the second differential signal by performing an addition process for adding the second potential difference signal to the first potential difference signal.

Figure 9A:
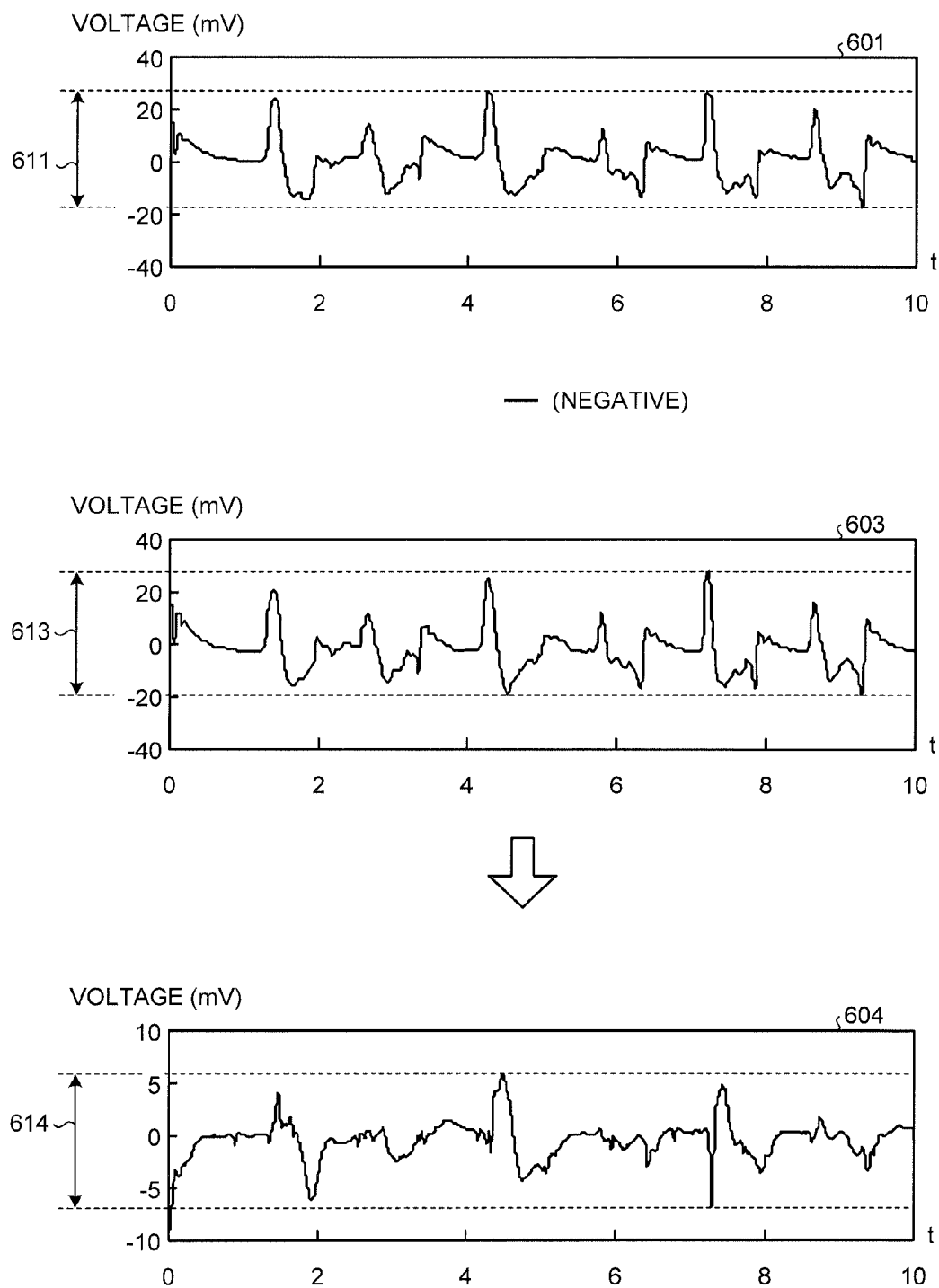
FIG. 9A is a schematic diagram illustrating a subtraction process performed by the differential signal calculating unit according to the second embodiment.

The subtraction process and the addition process performed by the differential signal calculating unit 403 according to the second embodiment will be described with reference to FIGS. 9A and 9B. FIG. 9A is a schematic diagram illustrating a subtraction process performed by the differential signal calculating unit according to the second embodiment. FIG. 9B is a schematic diagram illustrating an addition process performed by the differential signal calculating unit according to the second embodiment. When the subtraction process is described with reference to FIG. 9A, a description will be given of a case, as an example, in which the second potential difference signal is subtracted from the first potential difference signal.

Reference numeral 604 denotes an example of the first differential signal obtained as the result of the subtraction process. Reference numeral 605 denotes an example of the second differential signal obtained as the result of the addition process. Reference numeral 614 denotes the amplitude of the first differential signal obtained as the result of the subtraction process. In reference numeral 604 or 605, the vertical axis indicates the value of the differential signal and the horizontal axis indicates the time axis. The amplitude of the first potential difference signal is about 10 mV in the example illustrated in the example in FIG. 9A. Reference numeral 615 denotes the amplitude of the second differential signal obtained as the result of the addition process and is equal to or greater than 20 mV illustrated in the example in FIG. 9B. Furthermore, the intensity of the potential difference signal that is obtained after the correction performed by the differential signal calculating unit 403 and that is used for the addition process or the subtraction process is about 40 mV.

FIG. 9A will be described here. As illustrated by reference numeral 601 or 603 in FIG. 9A, if the differential signal calculating unit 403 performs the subtraction process, the differential signal calculating unit 403 subtracts the corrected second potential difference signal from, for example, the first potential difference signal. Consequently, as illustrated by reference numeral 604 in FIG. 9A, the differential signal calculating unit 403 calculates the first differential signal.

FIG. 9B will be described here. As illustrated by reference numeral 601 or 603 in FIG. 9B, if the differential signal calculating unit 403 performs the addition process, the differential signal calculating unit 403 adds the corrected second potential difference signal to the first potential difference signal. Consequently, as illustrated by reference numeral 605 in FIG. 9B, the differential signal calculating unit 403 calculates the second differential signal. The purpose of performing the subtraction process and the addition process by the differential signal calculating unit 403 will be described later when an advantage of the second embodiment is described; therefore, the description thereof will be omitted here.

For the first differential signal and the second differential signal calculated by the differential signal calculating unit 403, the RMS re-calculating unit 404 calculates the intensity of the differential signal. For example, similarly to the RMS calculating unit 401, the RMS re-calculating unit 404 calculates the intensity of the potential difference signal by calculating the RMS using "mathematical formula 1" or "mathematical formula 2". For example, the RMS re-calculating unit 404 calculates the RMS of the first differential signal indicated by reference numeral 604 illustrated in FIG. 9A and calculates the RMS of the second differential signal indicated by reference numeral 605 illustrated in FIG. 9B. In the examples illustrated in reference numeral 614 in FIG. 9A or reference numeral 615 in FIG. 9B, the amplitude of the first differential signal is smaller than that of the second differential signal. Accordingly, the value of the RMS of the first differential signal is smaller than that of the second differential signal.

In the following, a description will be given of a case, as an example, in which the RMS re-calculating unit 404 calculates the intensity of the potential difference signal by using the same method used by the RMS calculating unit 401 unless otherwise stated; however, the present invention is not limited thereto. Specifically, the RMS re-calculating unit 404 and the RMS calculating unit 401 may also calculate the intensity of the potential difference signal by using different methods.

The output processing unit 405 outputs, from the output unit 205, a differential signal that is smaller than the other intensity of the potential difference signal calculated by the RMS re-calculating unit 404. Specifically, between the two differential signals obtained as the result of the subtraction process performed by the differential signal calculating unit 403, the output processing unit 405 outputs a differential signal that is smaller than the other calculated intensity of the potential difference signal.

For example, the output processing unit 405 outputs a differential signal to an identification apparatus that identifies the pulse or the heartbeat of the subject from the differential signal. Then, for example, the identification apparatus identifies the pulse or the heartbeat of the subject from the differential signal or measures the degree of wakefulness of the subject.

In the second embodiment, a description will be given of a case, as an example, in which the noise processing apparatus 200 is different from the identification apparatus; however, the present invention is not limited thereto. For example, the noise processing apparatus 200 may also be integrated with the identification apparatus. In such a case, the noise processing apparatus 200 further identifies the pulse or the heartbeat of the subject from the differential signal or further detects the physical state of the subject by using the state of the identified pulse or heartbeat of the subject. Furthermore, the noise processing apparatus 200 may also be a part of the identification apparatus. In such a case, the output processing unit 405 outputs a differential signal to another unit, from among the units included in the identification apparatus, that identifies the pulse or the heartbeat of the subject from the differential signal.

Furthermore, the differential signal that is output by the output processing unit 405 is a potential difference signal indicating the potential difference between the steering wheel electrode 201 and the upper-part seat electrode 202 and is a potential difference signal between the electrodes that are brought into contact with the two locations separated by the heart.

Figure 10:
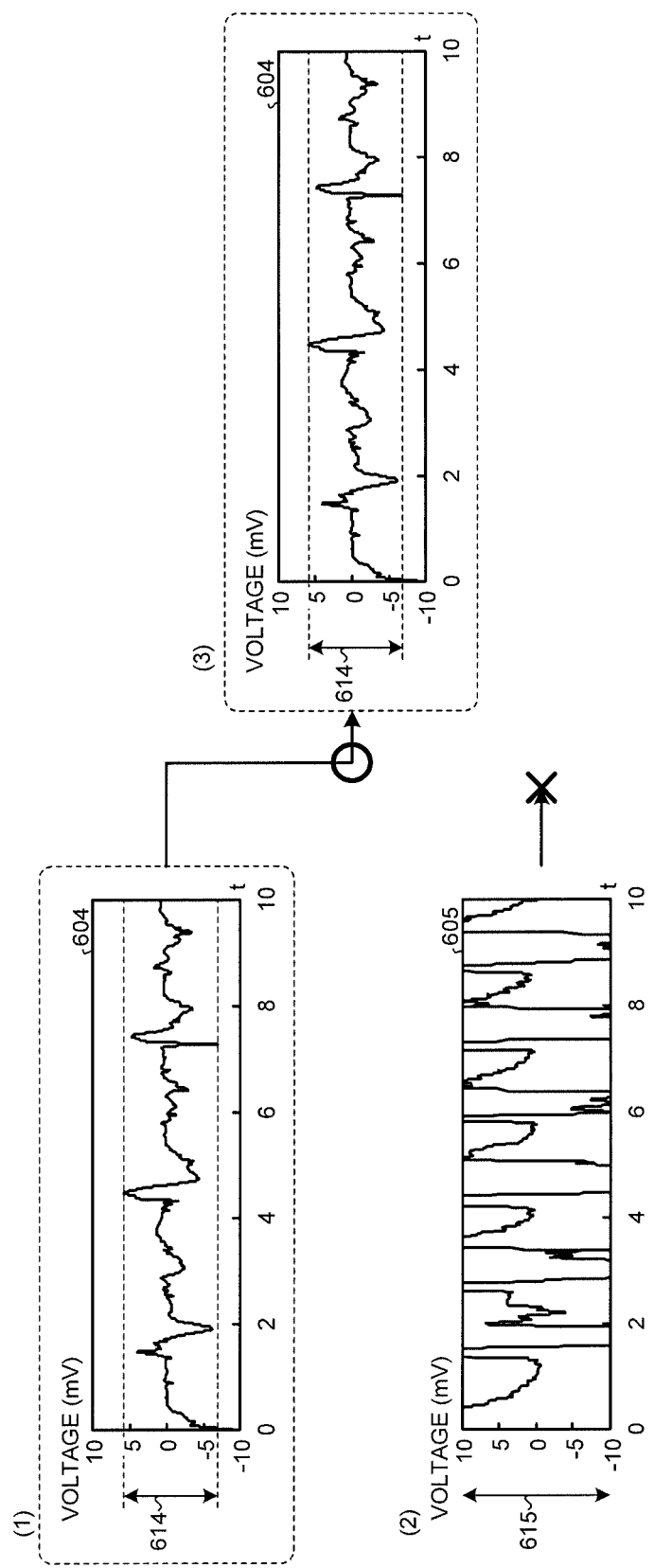
FIG. 10 is a schematic diagram illustrating a process performed by an output processing unit according to the second embodiment.

A process performed by the output processing unit 405 according to the second embodiment will be described with reference to FIG. 10 here. FIG. 10 is a schematic diagram illustrating a process performed by a output processing unit 405 according to the second embodiment. The symbol (1) illustrated in FIG. 10 indicates the first differential signal, the symbol (2) illustrated in FIG. 10 indicates the second differential signal, and the symbol (3) illustrated in FIG. 10 indicates the potential difference signal that is output by the output processing unit 405. In (1) to (3) illustrated in FIG. 10, the vertical axis indicates the value of the electric potential and the horizontal axis indicates the time axis.

As illustrated in (1) and (2) of FIG. 10, the output processing unit 405 compares the intensity of the first differential signal with the intensity of the second differential signal. At this time, the value of the RMS of the first differential signal is smaller than that of the second differential signal. Accordingly, as illustrated in (3) of FIG. 10, the output processing unit 405 selects the first differential signal and outputs the selected first differential signal.

As described above, the differences that are used when the differential signal calculating unit 403 performs the correction differ depending on predetermined intervals. Accordingly, the differential signals that are output by the output processing unit 405 are not always the same. For example, if the output processing unit 405 outputs the first differential signal at a certain time, the output processing unit 405 does not always output the first differential signal at another time; and there may be a case in which the output processing unit 405 outputs the second differential signal.

Furthermore, it is assumed that the two differential signals contain a heartbeat signal having the same intensity. Furthermore, although depending on the contact state of the subject and the electrode, the noise intensity contained in the potential difference signal is greater than the intensity of the heartbeat signal.

Figure 11:
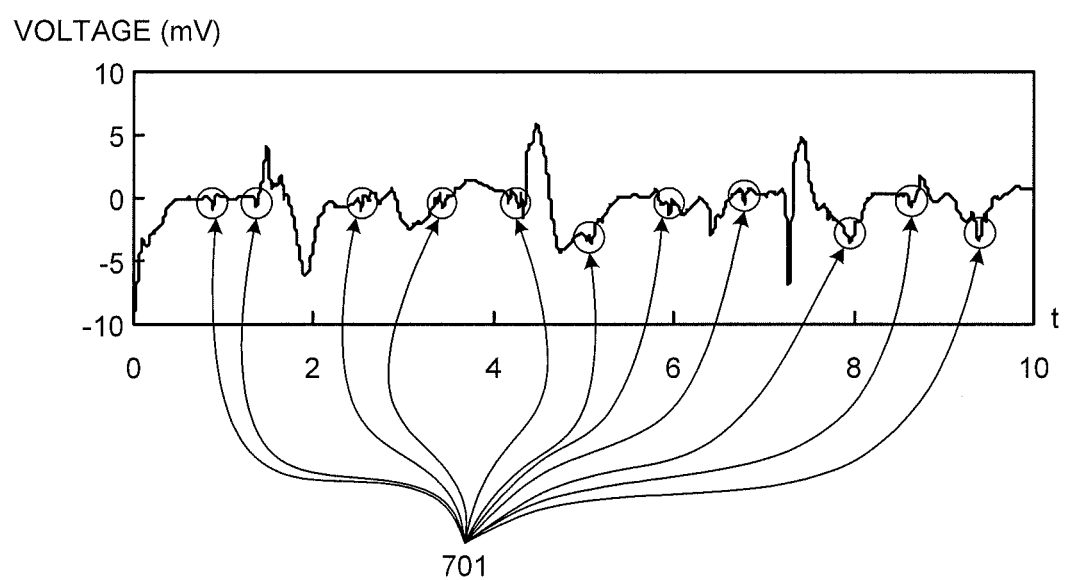
FIG. 11 is a schematic diagram illustrating an example of heartbeat signals contained in a differential signal.

An example of the heartbeat signal contained in the differential signal will be described here with reference to FIG. 11. FIG. 11 is a schematic diagram illustrating an example of heartbeat signals contained in a differential signal. The differential signal illustrated in FIG. 11 is an example of the differential signal that is output by the output processing unit 405. In FIG. 11, the vertical axis indicates the value of the differential signal and the horizontal axis indicates the time axis. Reference numeral 701 illustrated in FIG. 11 denotes arrows each indicating the heartbeat signal contained in the differentials signal. As illustrated by each of the arrows indicated by the reference numeral 701 in FIG. 11, the percentage of the intensities of the heartbeat signal occupied is smaller than the noise intensity from among the intensities of the differential signal.

Accordingly, it is assumed that the difference between the intensities of the two differential signals corresponds to the difference between the noise intensities contained in the two differential signals. Specifically, even if the output processing unit 405 outputs a differential signal by simply selecting the differential signal with the smaller intensity, the output processing unit 405 can outputs the differential signal containing the smaller noise intensity between the two differential signals.

Figure 12:
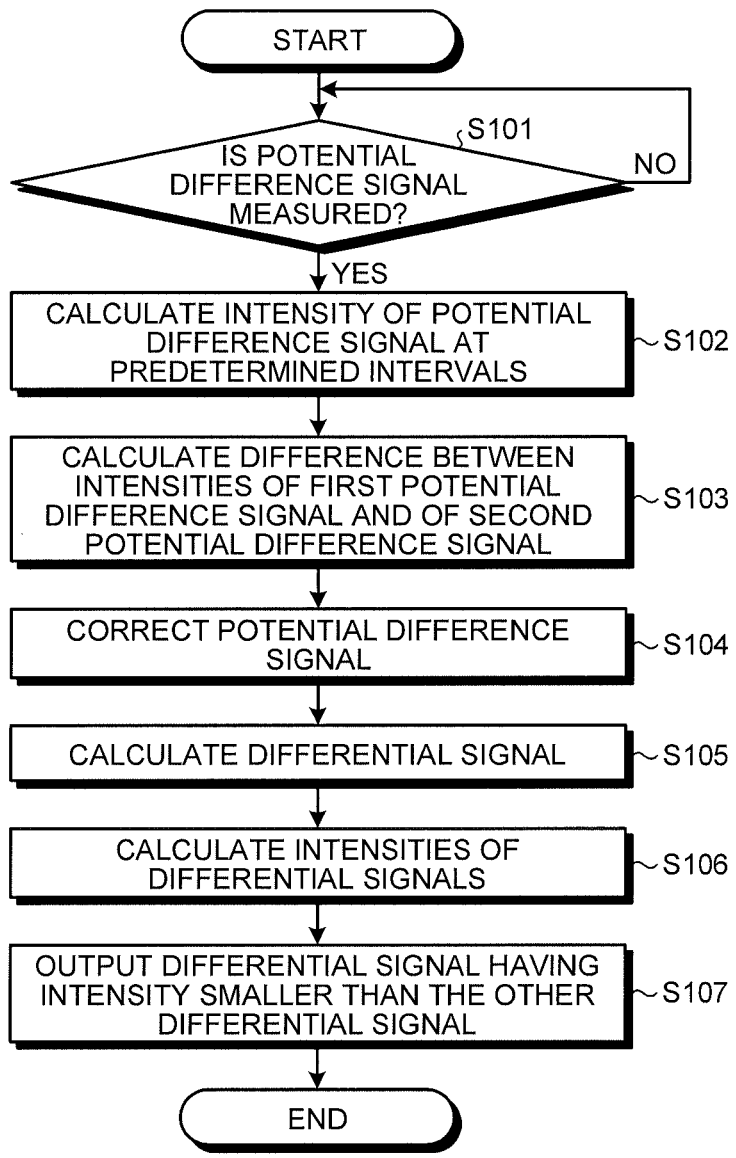
FIG. 12 is a flowchart illustrating the flow of a process performed by the noise processing apparatus according to the second embodiment.

Process Performed by the Noise Processing Apparatus According to the Second Embodiment In the following, the flow of a process performed by the noise processing apparatus 200 according to the second embodiment will be described with reference to FIG. 12. FIG. 12 is a flowchart illustrating the flow of a process performed by the noise processing apparatus according to the second embodiment. In the following, a description will be given of a case, as an example, in which the amplification factor calculating unit 402 calculates the difference by dividing the intensity of the first potential difference signal by the intensity of the second potential difference signal. Furthermore, a description will be given of a case, as an example, in which the differential signal calculating unit 403 corrects the second potential difference signal by using the difference calculated by the amplification factor calculating unit 402. Furthermore, a description will be given of a case, as an example, in which the value of the RMS of the first differential signal is smaller than that of the second differential signal.

As illustrated in FIG. 12, if a potential difference signal is measured by the electric potential measuring unit 204 (Yes at Step S101), i.e., if the first potential difference signal or the second potential difference signal is measured, the RMS calculating unit 401 calculates the intensity of the potential difference signal at predetermined intervals (Step S102). For example, the RMS calculating unit 401 calculates each of the RMSs of the first potential difference signal and the second potential difference signal.

Then, the amplification factor calculating unit 402 calculates the difference between the intensity of the first potential difference signal and the intensity of the second potential difference signal (Step S103). For example, the amplification factor calculating unit 402 divides the calculated RMS of the first potential difference signal by the calculated RMS of the second potential difference signal to calculate a difference of "1.49".

Then, the differential signal calculating unit 403 corrects the second potential difference signal such that the intensity of the first potential difference signal becomes the same as that of the second potential difference signal (Step S104). For example, the differential signal calculating unit 403 multiplies the second potential difference signal by "1.49" and defines the multiplication result of the potential difference signal as the corrected second potential difference signal.

Then, by using the corrected potential difference signal, the differential signal calculating unit 403 calculates, at predetermined intervals, a differential signal indicating the difference between the first potential difference signal and the second potential difference signal (Step S105). For example, by subtracting the corrected second potential difference signal from the first potential difference signal, the differential signal calculating unit 403 calculates the first differential signal. Furthermore, for example, by adding the corrected second potential difference signal to the first potential difference signal, the differential signal calculating unit 403 calculates the second differential signal.

Then, for the first differential signal and the second differential signal calculated by the differential signal calculating unit 403, the RMS re-calculating unit 404 calculates the intensity of each of the differential signals (Step S106). For example, the RMS re-calculating unit 404 calculates the RMS as the intensity of the differential signal.

Then, the output processing unit 405 outputs, from the output unit 205, the differential signal having the intensity that is smaller than that calculated by the RMS re-calculating unit 404 (Step S107). At this time, the value of the RMS of the first differential signal is smaller than that of the second differential signal and the output processing unit 405 outputs the first differential signal.

Advantage of the Second Embodiment

As described above, according to the second embodiment, the noise processing apparatus 200 measures the first potential difference signal and the second potential difference signal. Then, the noise processing apparatus 200 calculates, at predetermined intervals, the intensities of the first potential difference signal and the second potential difference signal. The noise processing apparatus 200 then calculates the difference between the intensities of the first potential difference signal and the second potential difference signal that are calculated at predetermined intervals. Then, by using the calculated difference, the noise processing apparatus 200 corrects, at predetermined intervals, the first potential difference signal and the second potential difference signal such that the intensity of the first potential difference signal becomes the same as that of the second potential difference signal. Then, by using the corrected potential difference signal, the noise processing apparatus 200 calculates, at predetermined intervals, a differential signal and outputs the calculated differential signal. Therefore, according to the second embodiment, noise can be appropriately reduced from the potential difference signal between electrodes that are brought into contact with two positions separated by the heart.

Figure 13A:
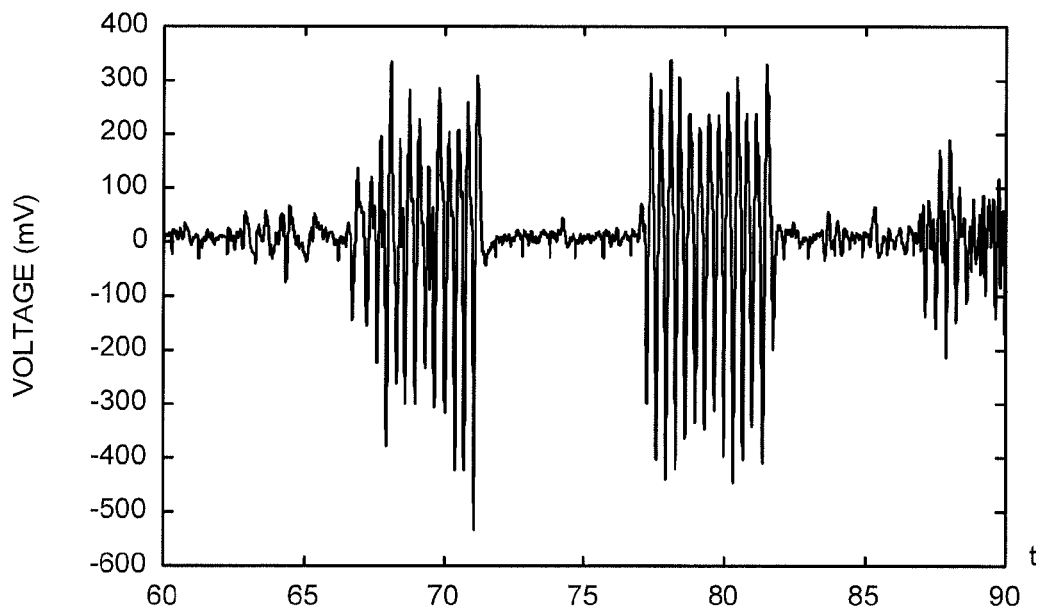
FIG. 13A is a schematic diagram illustrating an example of an advantage of the second embodiment.
Figure 13B:
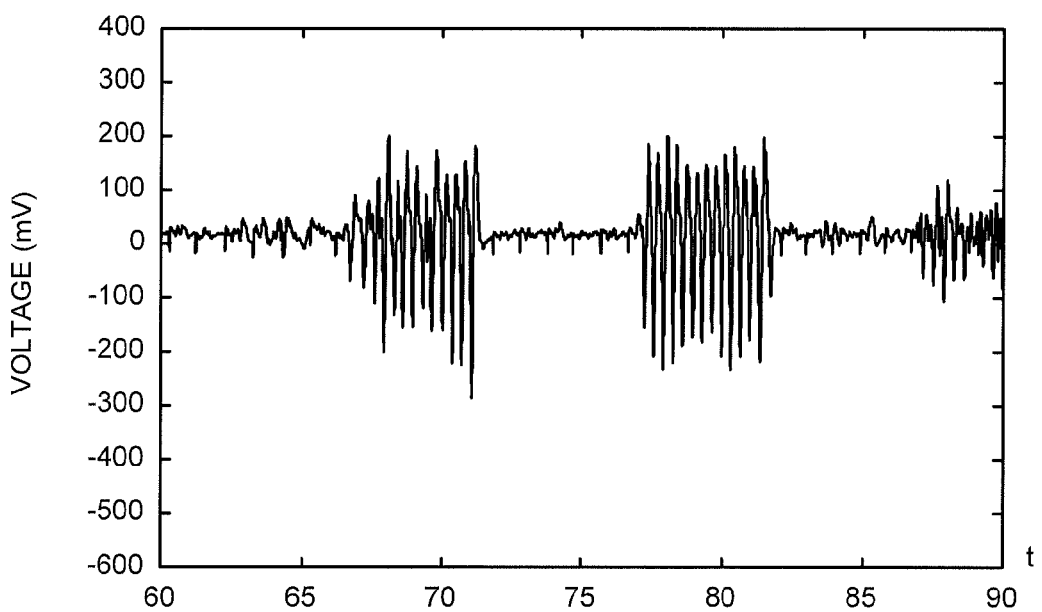
FIG. 13B is a schematic diagram illustrating an example of an advantage of the second embodiment.
Figure 13C:
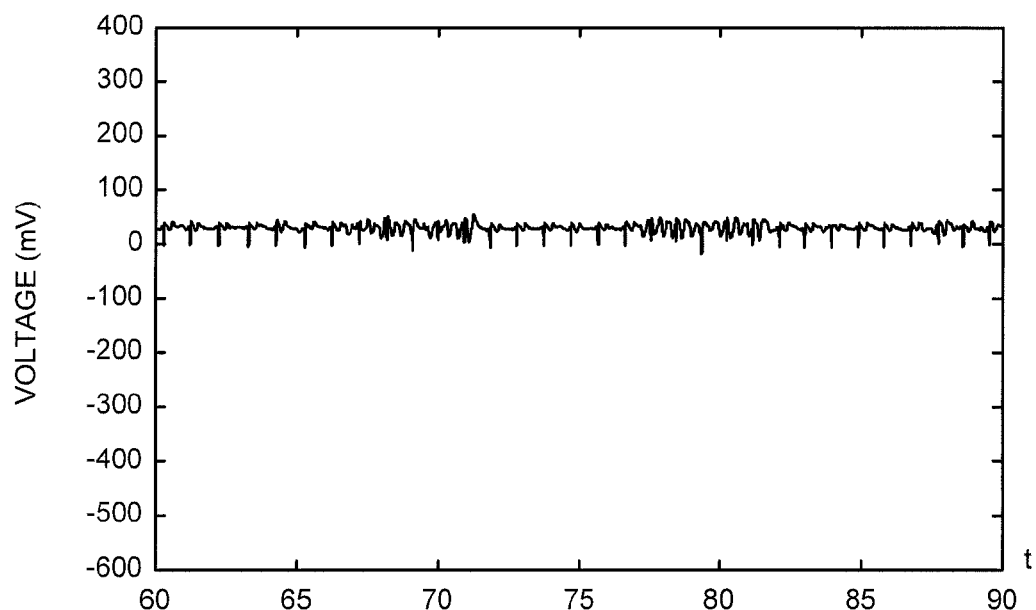
FIG. 13C is a schematic diagram illustrating an example of an advantage of the second embodiment.

For example, an advantage of the second embodiment will be described here with reference to FIGS. 13A, 13B, and 13C. FIGS. 13A, 13B, and 13C are schematic diagrams illustrating an example of an advantage of the second embodiment. FIG. 13A illustrates an example of the first potential difference signal or the second potential difference signal. FIG. 13B illustrates an example of a signal obtained when the correction is performed such that the intensity of the first potential difference signal and the second potential difference signal are not the same and when the second potential difference signal is simply subtracted from the first potential difference signal. FIG. 13C illustrates an example of a differential signal that is output by the output processing unit 405 according to the second embodiment. In FIGS. 13A to 13C, the vertical axis indicates the value of the potential difference signal or the differential signal and the horizontal axis indicates the time axis. In this case, the RMS in FIG. 13A is 186 mV, the RMS in FIG. 13B is 105 mV, and the RMS in FIG. 13C is 10.4 mV.

When comparing the RMS in FIG. 13A with the RMS in FIG. 13B, the RMS is reduced from 186 mV to 105 mV. In contrast, when comparing the RMS in FIG. 13A with the RMS in FIG. 13C, the RMS is reduced from 186 mV to 10.4 mV. Specifically, in the second embodiment, with a focus on that fact that a change in the impedance of the steering wheel electrode 201 is different from that of the upper-part seat electrode 202, the difference is calculated after performing the correction such that the intensities of the two potential difference signals are the same. Therefore, according to the second embodiment, when compared with a case of the correction such that the intensities of the two potential difference signals are not the same, an advantage is provided in that noise reduction increases.

Furthermore, according to the second embodiment, the noise processing apparatus 200 calculates the first differential signal by performing the subtraction process for subtracting the second potential difference signal from the first potential difference signal or subtracting the first potential difference signal from the second potential difference signal. Furthermore, the noise processing apparatus 200 calculates the second differential signal by performing the addition process by adding the second potential difference signal to the first potential difference signal. Then, the noise processing apparatus 200 calculates each of the intensities of the calculated first differential signal and the second differential signal and outputs a differential signal having a smaller intensity. Therefore, according to the second embodiment, even if the phase of the first potential difference signal is different from that of the second potential difference signal, noise can be reduced.

In the following, the purpose of performing the subtraction process and the addition process by the differential signal calculating unit 403 will be described. The electrode is sometimes brought into contact with the subject via the clothes that the subject is wearing. For example, the upper-part seat electrode 202 is brought into electrical contact with the subject via a skirt or jeans. Furthermore, the steering wheel electrode 201 is sometimes brought into electrical contact with the subject via, as a part of the clothes, gloves, an adhesive bandage, a bandage, and the like. Static electricity is generated in the clothes due to friction between the subject and the clothes or friction between the clothes and the electrode. Furthermore, the polarity of the static electricity generated in the clothes differs depending on the clothes that the subject is wearing. If the polarity of the static electricity differs, the phase of the potential difference signal obtained from the electrode differs.

Figure 14:
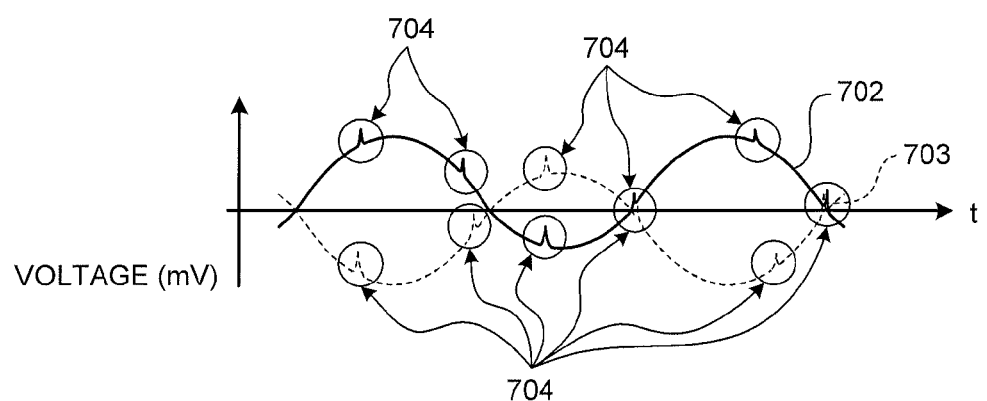
FIG. 14 is a schematic diagram illustrating the relationship between the polarity and phase of a potential difference signal.

The relationship between a polarity and a phase of the potential difference signal will be described here with reference to FIG. 14. FIG. 14 is a schematic diagram illustrating the relationship between the polarity and the phase of a potential difference signal. In FIG. 14, reference numeral 702 denotes an example of the potential difference signal having positive polarity. Reference numeral 703 denotes an example of the potential difference signal having negative polarity. Reference numeral 704 denotes the heartbeat signal contained in the potential difference signal. Furthermore, in reference numeral 702 or 703 in FIG. 14, from among the intensities of the potential difference signals, a portion other than the intensity associated with the heartbeat signal is the noise intensity.

As illustrated in FIG. 14, the phases of the potential difference signals are opposite each other between cases in which the polarity thereof is positive and negative. Accordingly, if the phases of the two potential difference signals differ and if the difference between the two potential difference signals is calculated, the noise contained in the differential signal does not decrease at all but actually increases. For example, if the differential signal is calculated by subtracting the potential difference signal, which is calculated when the polarity of the signal is negative, from the potential difference signal, which is calculated when the polarity of the signal is positive, the noise intensity contained in the calculated differential signal is greater than the noise intensity contained in the potential difference signal.

If the phases of the two potential difference signals differ, it is assumed that noise can be reduced by calculating the sum of the two potential difference signals. Specifically, it is assumed that the noise intensity in the differential signal that is obtained by calculating the sum of the two potential difference signals is smaller than the noise intensity of the potential difference signal.

In light of the circumstances described above, according to the second embodiment, the first differential signal and the second differential signal are calculated by performing the addition process and the subtraction process and outputs the differential signal having the intensity smaller than the other differential signal between the calculated differential signals. Accordingly, the noise can be reduced regardless of the phase of the potential difference signal.

[c] Third Embodiment

In a third embodiment, a description will be given of a case in which the RMS calculating unit 401 calculates, at different predetermined intervals, the intensity of the potential difference signal in accordance with the state of the first potential difference signal or the second potential difference signal. For example, a description will be given of a case in which the RMS calculating unit 401 calculates, in accordance with the first potential difference signal or the second potential difference signal, the intensity of the potential difference signal at predetermined intervals, e.g., at 3-second intervals or at 5-second intervals.

In the third embodiment, a case will be described of using, as an example of the state of the first potential difference signal or the second potential difference signal, the intensity or the waveform of the potential difference signal. In the following, a description of components that are identical to those of the noise processing apparatus according to the second embodiment will be omitted.

Figure 15:
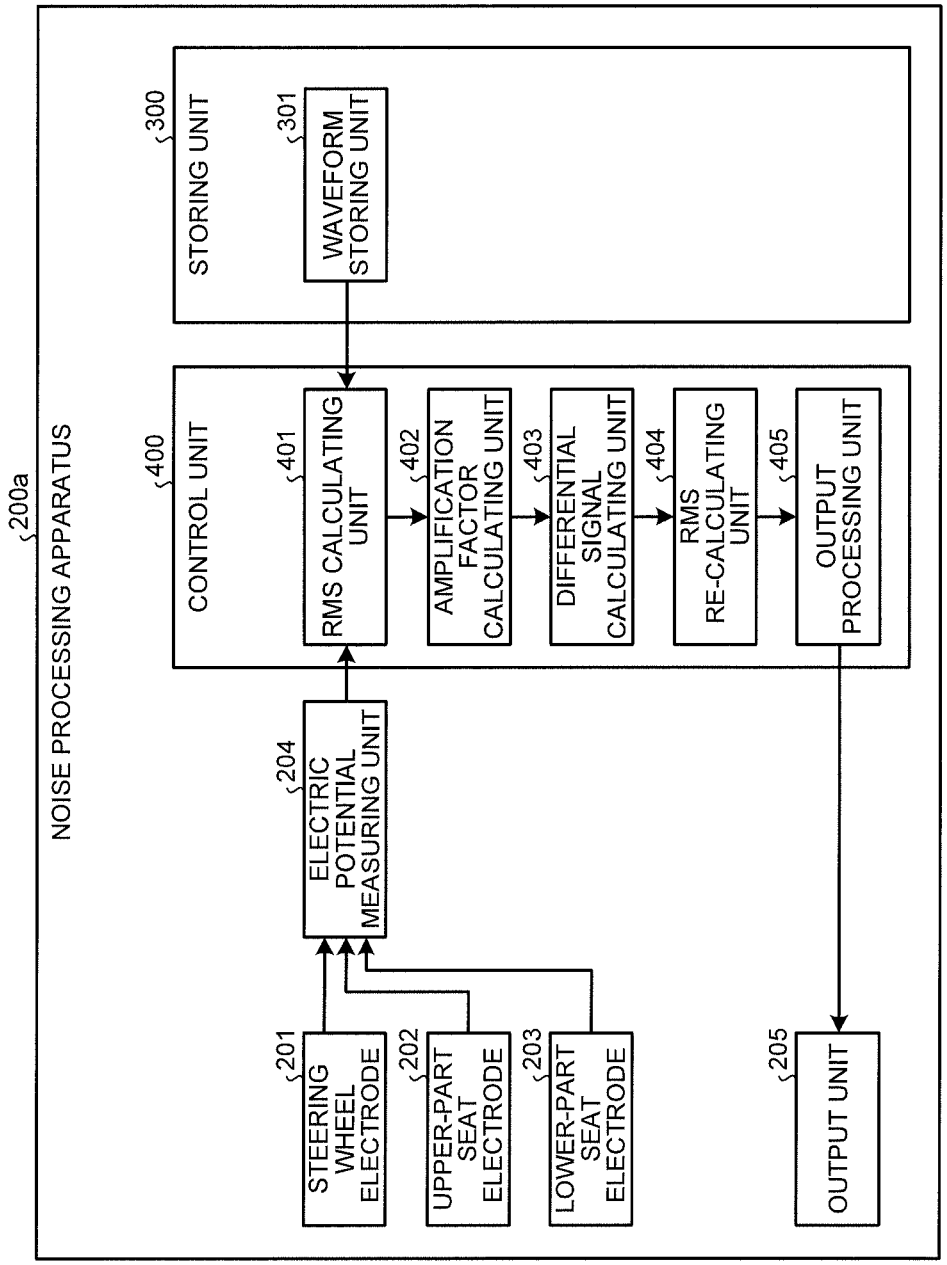
FIG. 15 is a block diagram illustrating an example configuration of a noise processing apparatus according to a third embodiment.

Configuration of the Noise Processing Apparatus According to the Third Embodiment In the following, a configuration example of a noise processing apparatus 200a according to the third embodiment will be described with reference to FIG. 15. FIG. 15 is a block diagram illustrating an example configuration of a noise processing apparatus according to a third embodiment. As illustrated in FIG. 15, the noise processing apparatus 200a further includes a waveform storing unit 301 in addition to the units included in the noise processing apparatus 200 that has been described using FIG. 2.

Figure 16:
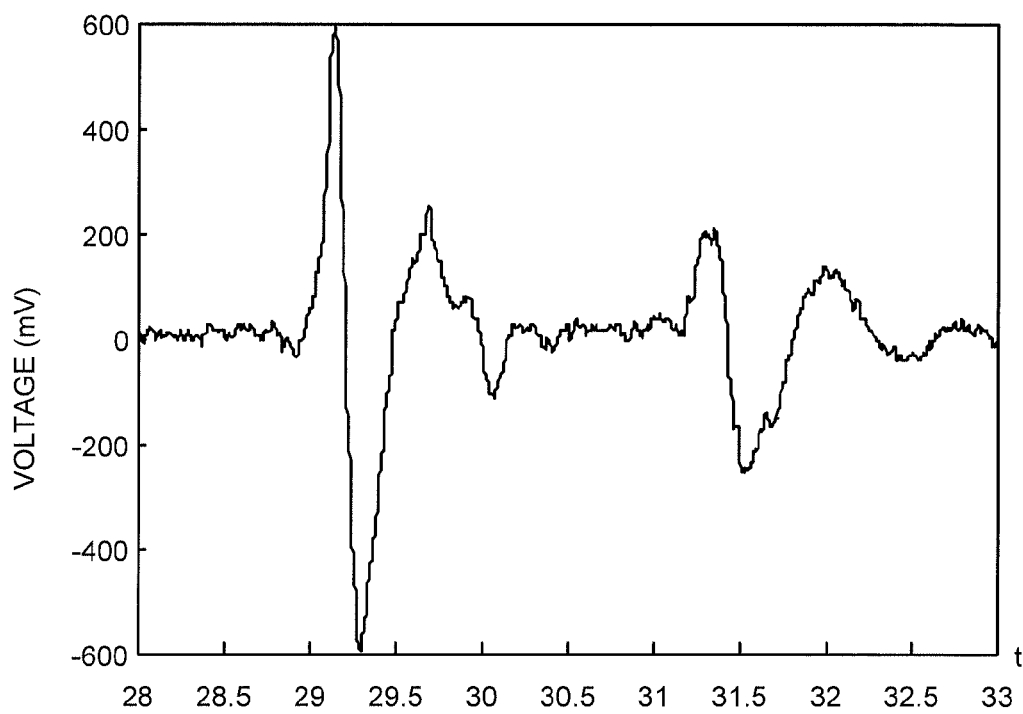
FIG. 16 is a schematic diagram illustrating an example of a waveform of a potential difference signal stored by a waveform storing unit according to the third embodiment.

The waveform storing unit 301 stores therein an interval by associating it with the waveform of the potential difference signal. Information stored by the waveform storing unit 301 is used by the RMS calculating unit 401. An example of the waveform of the potential difference signal stored by the waveform storing unit 301 according to the third embodiment will be described with reference to FIG. 16. FIG. 16 is a schematic diagram illustrating an example of a waveform of a potential difference signal stored by a waveform storing unit according to the third embodiment. FIG. 16 illustrates an example of the potential difference signal measured when the subject sits down again. In FIG. 16, the vertical axis indicates the value of the potential difference signal and the horizontal axis indicates the time axis. In the example illustrated in FIG. 16, when the subject sits down again, the value of the potential difference signal varies locally and significantly.

The waveform storing unit 301 stores therein intervals shorter than those obtained when the waveform of the potential difference signal does not vary locally and significantly by associating the intervals with the waveform of the potential difference signal illustrated in FIG. 16. For example, the waveform storing unit 301 stores therein "2 seconds" by associating it with the waveform of the potential difference signal illustrated in FIG. 16.

Figure 17:
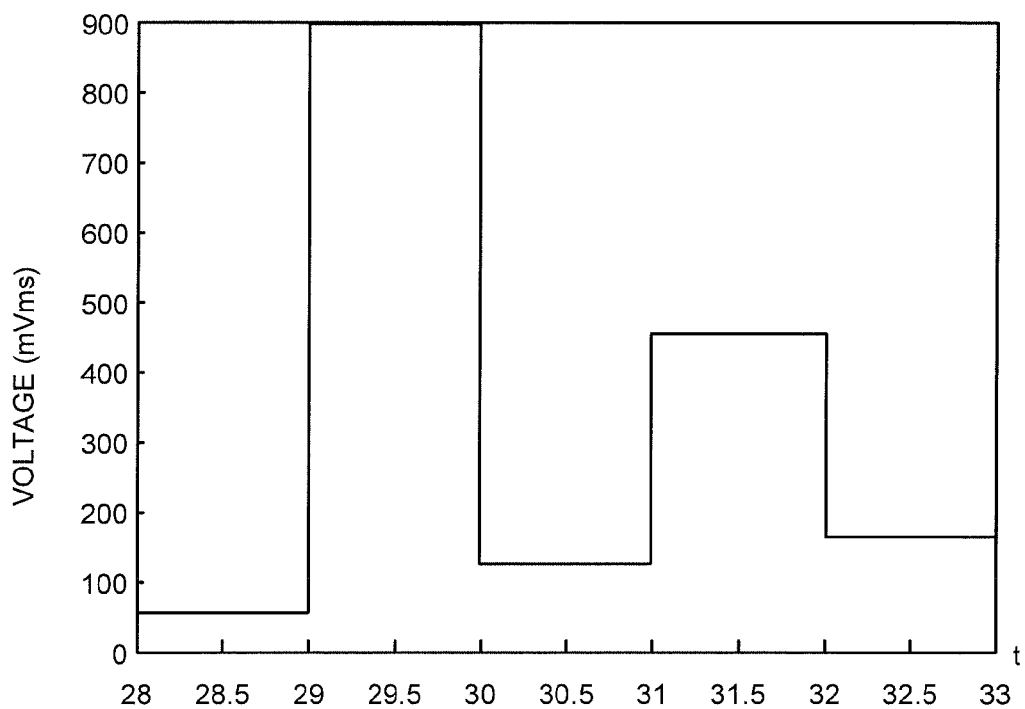
FIG. 17 is a schematic diagram illustrating an interval associated with the waveform of the potential difference signal illustrated in FIG. 16.

The interval associated with the waveform of the potential difference signal illustrated in FIG. 16 will be described here with reference to FIG. 17. FIG. 17 is a schematic diagram illustrating an interval associated with the waveform of the potential difference signal illustrated in FIG. 16. FIG. 17 illustrates an example of the RMS calculated from the potential difference signal illustrated in FIG. 16. In FIG. 17, the vertical axis indicates the value of the RMS and the horizontal axis indicates the time axis. The horizontal axis illustrated in FIG. 17 is associated with that illustrated in FIG. 16.

If the subject sits on the seat again, the value of the potential difference signal varies locally and significantly. Accordingly, as illustrated in FIG. 17, if the subject sits down again, the value of the RMS also varies locally and significantly. When calculating the RMS of both a portion in which values vary locally and significantly and a portion in which values do not vary locally and significantly, the calculated value of the RMS becomes small at the portion in which the value of the potential difference signal varies locally and significantly, whereas the calculated value of the RMS becomes large at the portion in which the value of the potential difference signal does not vary locally and significantly. Accordingly, from among the potential difference signals, for the portion in which the value of the potential difference signal varies locally and significantly, the RMS is preferably calculated using a portion in which the value of the potential difference signal varies significantly without using a portion in which the value of the potential difference signal does not vary locally. Furthermore, from among the potential difference signals, for the portion in which the value of the potential difference signal does not vary locally and significantly, the RMS is preferably calculated using a portion in which the value of the potential difference signal does not vary locally and significantly without using a portion in which the value of the potential difference signal varies significantly. Because the waveform storing unit 301 stores therein a short interval by associating it with the waveform of the potential difference signal illustrated in FIG. 16, as will be described later, the RMS calculating unit 401 can calculate the RMS by distinguishing the portion in which the value varies locally and significantly from the portion in which the value does not vary locally and significantly.

In the following, a description will be given of a case in which the waveform storing unit 301 stores therein "2 seconds" by associating it with a waveform of the potential difference signal illustrated in FIG. 16; however, the present invention is not limited thereto. For example, the waveform storing unit 301 may also store therein a value indicating an interval shorter than 2 seconds, longer than 2 seconds, or an arbitrary value. In such a case, as a stored value associated with the waveform of the potential difference signal, it is assumed that the time intervals of the waveform of the potential difference signal will be used. In the example illustrated in FIG. 16, the characteristic waveform, i.e., the pattern of the waveform, is detected during the one second between 29 and 30 on the horizontal axis and during the one second between 31 and 32 on the horizontal axis. Accordingly, as a value that is stored and is associated with the waveform of the potential difference signal, it is possible to store one second, which is an interval of one second between 29 and 30 and between 31 and 32, by associating the interval with the waveform. Alternatively, if all of the waveforms illustrated in FIG. 16 are detected from a series of the operations, 3 seconds between 29 and 32 may also be associated with the waveform. The local and large variation in the potential difference signal can be assumed to be the operation time performed by the subject. In this way, by using time intervals from which a pattern waveform is obtained in accordance with the pattern waveform associated with a series of the operations performed by the subject, it is possible to set an interval that is used to calculate the RMS according to the time taken for the operation by the subject.

Furthermore, in the following, a case will be described in which the waveform storing unit 301 stores therein an interval by associating it with the waveform of the potential difference signal; however, the present invention is not limited thereto. For example, the waveform storing unit 301 may also store therein information used for shortening or lengthening the interval by associating it with the waveform of the potential difference signal.

The RMS calculating unit 401 according to the third embodiment calculates, at different predetermined intervals, the intensity of the potential difference signal in accordance with the state of the first potential difference signal or the second potential difference signal. Specifically, the RMS calculating unit 401 calculates, at different predetermined intervals, the intensity of the potential difference signal in accordance with the waveform or the intensity of the first potential difference signal or the second potential difference signal.

In the following, a description will be given of a case in which the operation is performed in accordance with the waveform of the first potential difference signal or the second potential difference signal. The RMS calculating unit 401 calculates the intensity of the potential difference signal at different predetermined intervals in accordance with the pattern of the waveform of the first potential difference signal or the second potential difference signal. For example, the RMS calculating unit 401 determines whether the waveform of the first potential difference signal or the second potential difference signal matches the waveform of the potential difference signal stored in the waveform storing unit 301. Then, if the RMS calculating unit 401 determines that they match, the RMS calculating unit 401 reads, from the waveform storing unit 301, the information associated with the matched waveform of the potential difference signal. Then, the RMS calculating unit 401 changes the interval in accordance with the read information.

In the following, a case will be described in detail in which "5 seconds" is used as an interval. If the RMS calculating unit 401 determines that the waveform pattern of the first potential difference signal or the second potential difference signal matches the waveform of the potential difference signal illustrated in FIG. 16, the RMS calculating unit 401 reads "2 seconds" from the waveform storing unit 301. Then, the RMS calculating unit 401 changes the interval from "5 seconds" to "2 seconds". Accordingly, after that, the RMS calculating unit 401 calculates, at two-second intervals, the intensity of the potential difference signal by using the potential difference signal during the 2 seconds before the process time begins.

In the following, a description will be given of a case in which the operation is performed in accordance with the intensity of the first potential difference signal or the second potential difference signal. If the intensity of the first potential difference signal or the second potential difference signal is smaller than a threshold in a predetermined time period, the RMS calculating unit 401 calculates the intensity by using an interval longer than that used in a case in which the intensity of the first potential difference signal or the second potential difference signal is not smaller than the threshold for a predetermined period. The threshold used by the RMS calculating unit 401 is also referred to as an intensity calculating threshold.

This will be further described in detail by using a case, as an example, in which the intensity calculating threshold is "200 mV", a predetermined period is "one minute", and an interval is "5 seconds". If the RMS calculating unit 401 obtains, as the calculation result, a value smaller than "200 mV", the RMS calculating unit 401 determines whether the value of the RMS is smaller than "200 mV" for one minute or more. Then, if the RMS calculating unit 401 determines that the value of the RMS is smaller than "200 mV" for one minute or more, the RMS calculating unit 401 changes the interval from "5 seconds" to "10 seconds". Consequently, after that, the RMS calculating unit 401 calculates, at 10-second intervals, the intensity of the potential difference signal by using the potential difference signal during the 10 seconds before the process time begins.

In the above description, a case has been described in which one minute is used as a predetermined period; however, the present invention is not limited thereto. For example, it is possible to use any time period, such as a time period shorter than one minute or a time period longer than one minute. Furthermore, in the above description, a case has been described in which the interval is changed from "5 seconds" to "10 seconds"; however, the present invention is not limited thereto. For example, the interval can be changed to an arbitrary value.

Furthermore, for example, if the intensity of the first potential difference signal or the second potential difference signal is greater than the threshold, the RMS calculating unit 401 calculates the intensity by using an interval shorter than that used in a case in which the intensity of the first potential difference signal and the second potential difference signal is not greater than the threshold.

This will be further described using a case, as an example, in which the intensity calculating threshold is "200 mV" and an interval is "5 seconds". The RMS calculating unit 401 determines whether, as the calculation result, the RMS calculating unit 401 obtains a value greater than "200 mV". Then, if the RMS calculating unit 401 determines that it obtains a greater value, the RMS calculating unit 401 changes the interval from "5 seconds" to "3 seconds". Consequently, after that, the RMS calculating unit 401 calculates, at three-second intervals, the intensity of the potential difference signal by using the potential difference signal during the 3 seconds before the process time begins.

Figure 18:
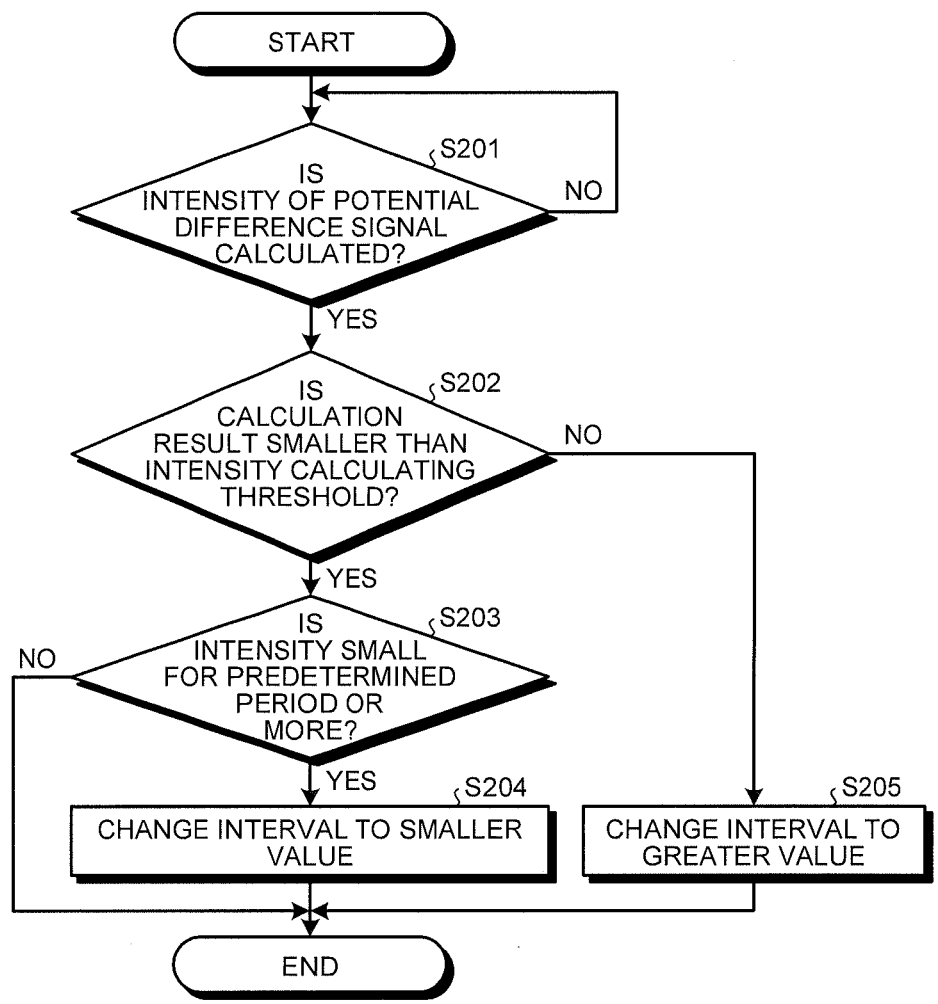
FIG. 18 is a flowchart illustrating the flow of an interval change process performed by the RMS calculating unit according to the third embodiment.

Process of Interval Change Performed by the RMS Calculating Unit 401 According to the Third Embodiment An example of the flow of the interval change process performed by the RMS calculating unit 401 according to the third embodiment will be described here with reference to FIG. 18. FIG. 18 is a flowchart illustrating the flow of an interval change process performed by the RMS calculating unit according to the third embodiment. In the following, a case will be described in which different predetermined intervals are used in accordance with the intensity of the first potential difference signal or the second potential difference signal. In the following, a description will be given of a case in which the intensity calculating threshold is "200 mV", a predetermined period is "one minute", and an interval is "5 seconds".

If the RMS calculating unit 401 calculates the intensity of the potential difference signal (Yes at Step S201), the RMS calculating unit 401 determines whether the calculation result is smaller than the intensity calculating threshold (Step S202). For example, the RMS calculating unit 401 determines whether the calculation result is smaller than "200 mV". If the RMS calculating unit 401 determines that the calculation result is smaller than "200 mV" (Yes at Step S202), the RMS calculating unit 401 determines whether the intensity of the potential difference signal is small for a predetermined period or more (Step S203). Then, if the RMS calculating unit 401 determines that the intensity is small for a predetermined period or more (Yes at Step S203), the RMS calculating unit 401 changes the interval to a smaller value (Step S204). For example, the RMS calculating unit 401 changes the interval from "5 seconds" to "3 seconds". Furthermore, if the RMS calculating unit 401 determines that the intensity is small for a predetermined period or more (No at Step S203), the RMS calculating unit 401 does not change the interval.

Furthermore, if the RMS calculating unit 401 determines that the calculation result is not smaller than the intensity calculating threshold (No at Step S202), i.e., determines that the calculation result is greater than the intensity calculating threshold, the RMS calculating unit 401 changes the interval to a greater value (Step S205). For example, the RMS calculating unit 401 changes the interval from "5 seconds" to "10 seconds".

Advantage of the Third Embodiment

As described above, according to the third embodiment, because the noise processing apparatus 200a calculates the intensity at different predetermined intervals in accordance with the state of the first potential difference signal or the second potential difference signal, noise contained in the potential difference signal can be appropriately reduced. For example, if a value of the RMS becomes greater, i.e., if the noise intensity contained in the potential difference signal becomes greater, the effect due to the noise can be promptly reduced by calculating the RMS after shortening the interval. Furthermore, if the value of the RMS is stable within the threshold, the number of calculations can be reduced by calculating the RMS after lengthening the interval.

[d] Fourth Embodiment

In a fourth embodiment, a case will be described in which a noise processing apparatus 200b is arranged in a vehicle and the intensity calculating threshold is changed in accordance with the speed of the vehicle. For example, as will be described below, a case will be described in which, if the speed of a vehicle is high, the RMS calculating unit 401 uses the value of "300 mV" as the intensity calculating threshold, whereas, if the speed of a vehicle is low, the RMS calculating unit 401 uses the value of "100 mV" as the intensity calculating threshold.

The purpose of changing the intensity calculating threshold in accordance with the speed will be briefly described here. It is assumed that the contact state between a subject and an electrode changes when the subject moves his/her body or an apparatus vibrates. Furthermore, the intensity of the potential difference signal changes due to the impedance of the electrode itself or the impedance of a contact portion between the electrode and the subject. As the impedance increases, the noise contained in the potential difference signal becomes strong, and thus the intensity of the potential difference signal also becomes strong. It is assumed that the impedance of the contact portion changes in accordance with the contact state between the electrode and the subject. Accordingly, the intensity of the noise contained in the potential difference signal changes due to vibrations of the vehicle or movement of the subject's body. Furthermore, it is assumed that the vibrations of the vehicle increases as the speed of the vehicle increases.

Figure 19A:
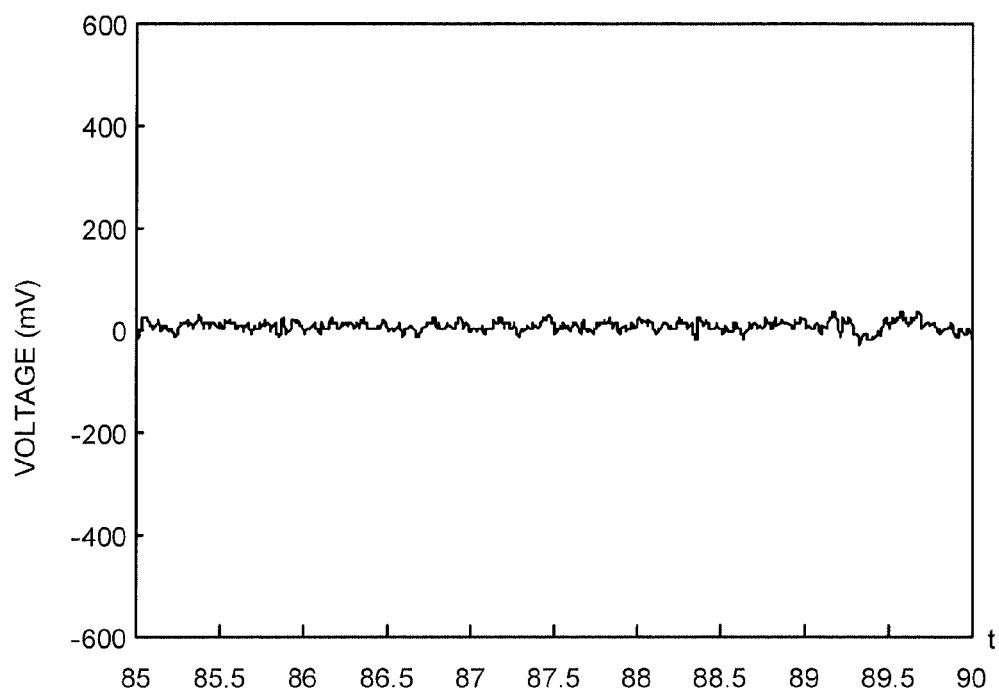
FIG. 19A is a schematic diagram illustrating an example of a potential difference signal measured when a vehicle is idling.
Figure 19B:
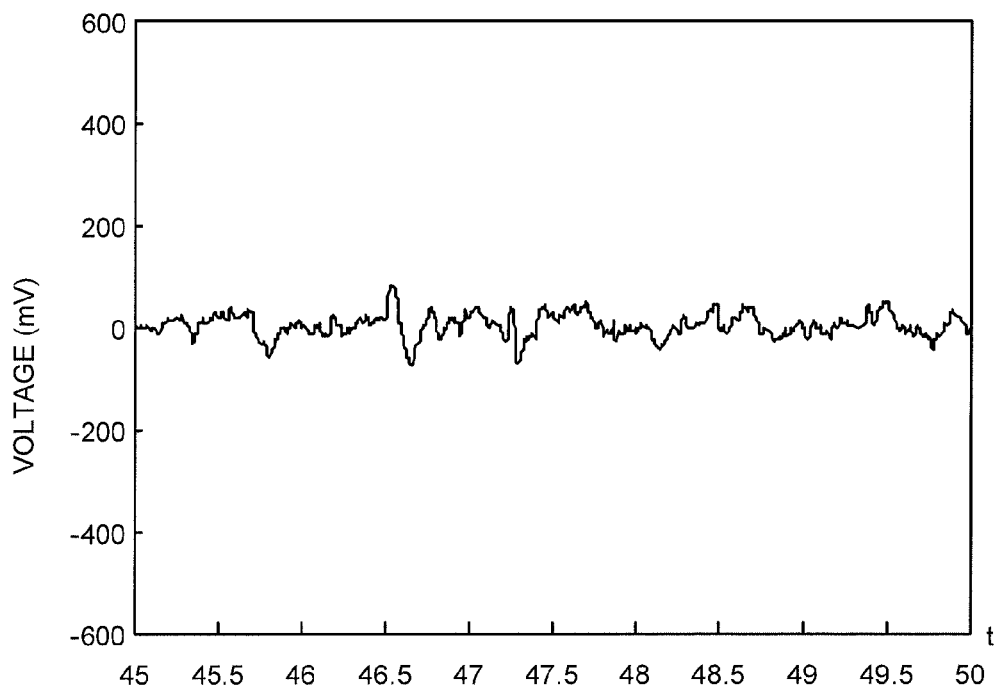
FIG. 19B is a schematic diagram illustrating an example of a potential difference signal measured when a vehicle is running on a general road.
Figure 19C:
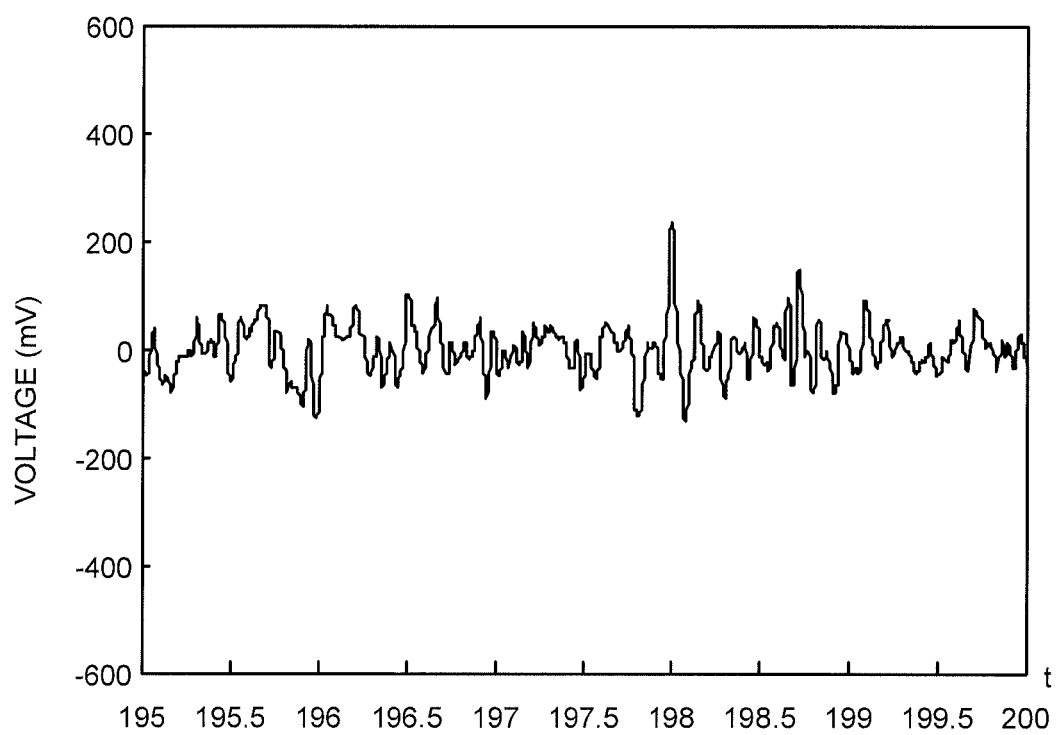
FIG. 19C is a schematic diagram illustrating an example of a potential difference signal measured when a vehicle is running on an expressway.
Figure 20A:
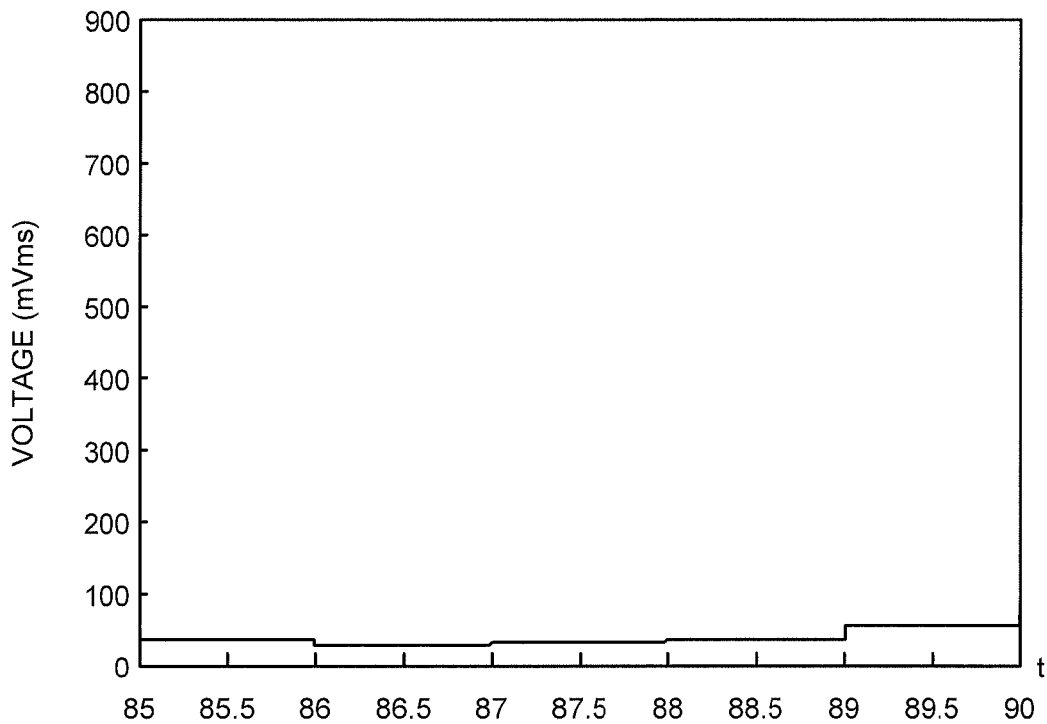
FIG. 20A is a schematic diagram illustrating an example of the RMS calculated when a vehicle is idling.
Figure 20B:
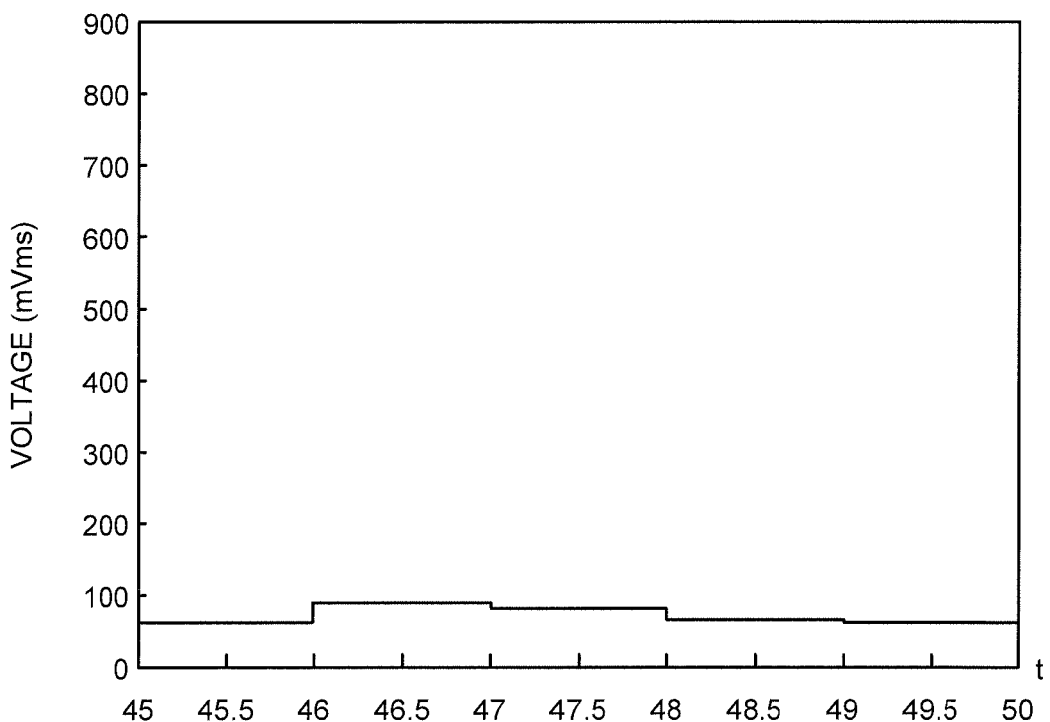
FIG. 20B is a schematic diagram illustrating an example of the RMS calculated when a vehicle is running on a general road.
Figure 20C:
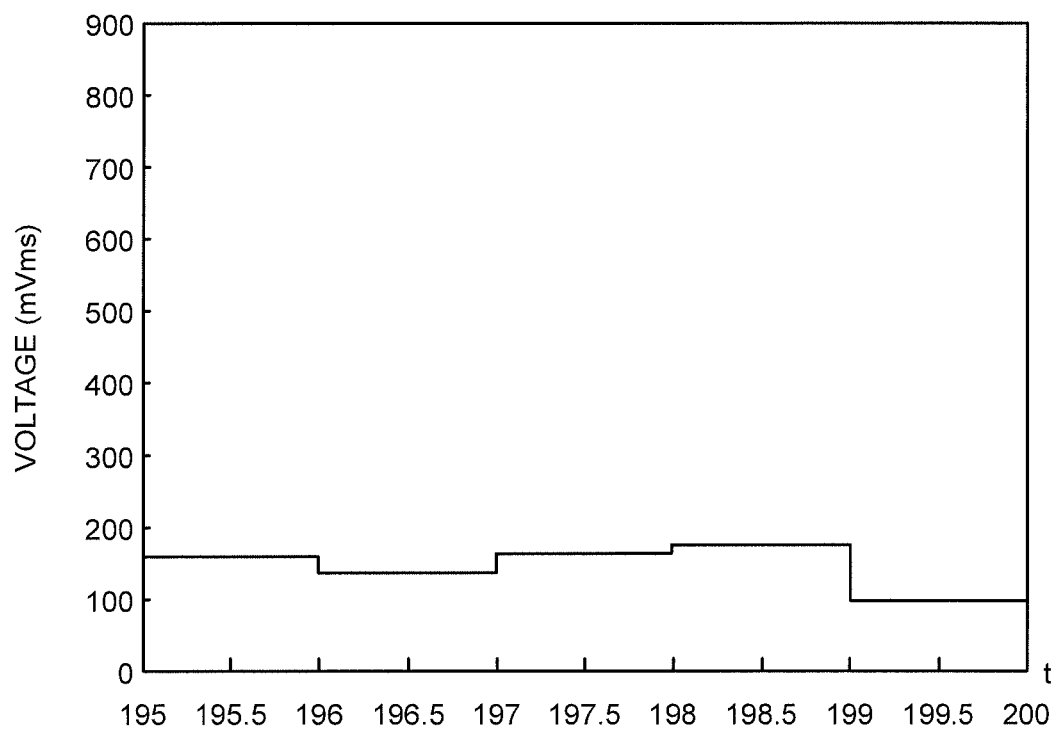
FIG. 20C is a schematic diagram illustrating an example of the RMS calculated when a vehicle is running on an expressway.

In the following, the relationship between the speed of a vehicle and the intensity of the potential difference signal will be described with reference to FIGS. 19A to 19C and 20A to 20C. FIG. 19A is a schematic diagram illustrating an example of a potential difference signal measured when a vehicle is idling. FIG. 19B is a schematic diagram illustrating an example of a potential difference signal measured when a vehicle is running on a general road. FIG. 19C is a schematic diagram illustrating an example of a potential difference signal measured when a vehicle is running on an expressway. FIG. 20A is a schematic diagram illustrating an example of the RMS calculated when a vehicle is idling. FIG. 20B is a schematic diagram illustrating an example of the RMS calculated when a vehicle is running on a general road. FIG. 20C is a schematic diagram illustrating an example of the RMS calculated when a vehicle is running on an expressway. In FIGS. 19A to 19C, the vertical axis indicates the value of the potential difference signal and the horizontal axis indicates the time axis. In FIGS. 20A to 20C, the vertical axis indicates the value of the RMS and the horizontal axis indicates the time axis. The horizontal axes illustrated in FIGS. 19A to 19C are associated with those illustrated in FIGS. 20A to 20C.

As illustrated in FIGS. 19A to 19C, the order of the magnitude of the amplitude of the potential difference signal is "when a vehicle is idling<when a vehicle is running on a general road<when a vehicle is running on an expressway". In other words, the amplitude of the potential difference signal obtained when a vehicle is running on an expressway is greater than that obtained when a vehicle is running on a general road, and the amplitude of the potential difference signal obtained when a vehicle is running on a general road is greater than that obtained when a vehicle is idling. Accordingly, as illustrated in FIGS. 20A to 20C, the order of the size of the RMS also becomes "idling<running on a general road<running on an expressway". In other words, the RMS obtained when a vehicle is running on an expressway is greater than that obtained when a vehicle is running on a general road and the RMS obtained when a vehicle is running on a general road is greater than that obtained when a vehicle is idling.

Accordingly, as will be described below, by changing the intensity calculating threshold in accordance with the vehicle speed, the noise processing apparatus 200b according to the fourth embodiment can determine an interval by using an appropriate intensity calculating threshold in accordance with the vehicle speed.

Figure 21:
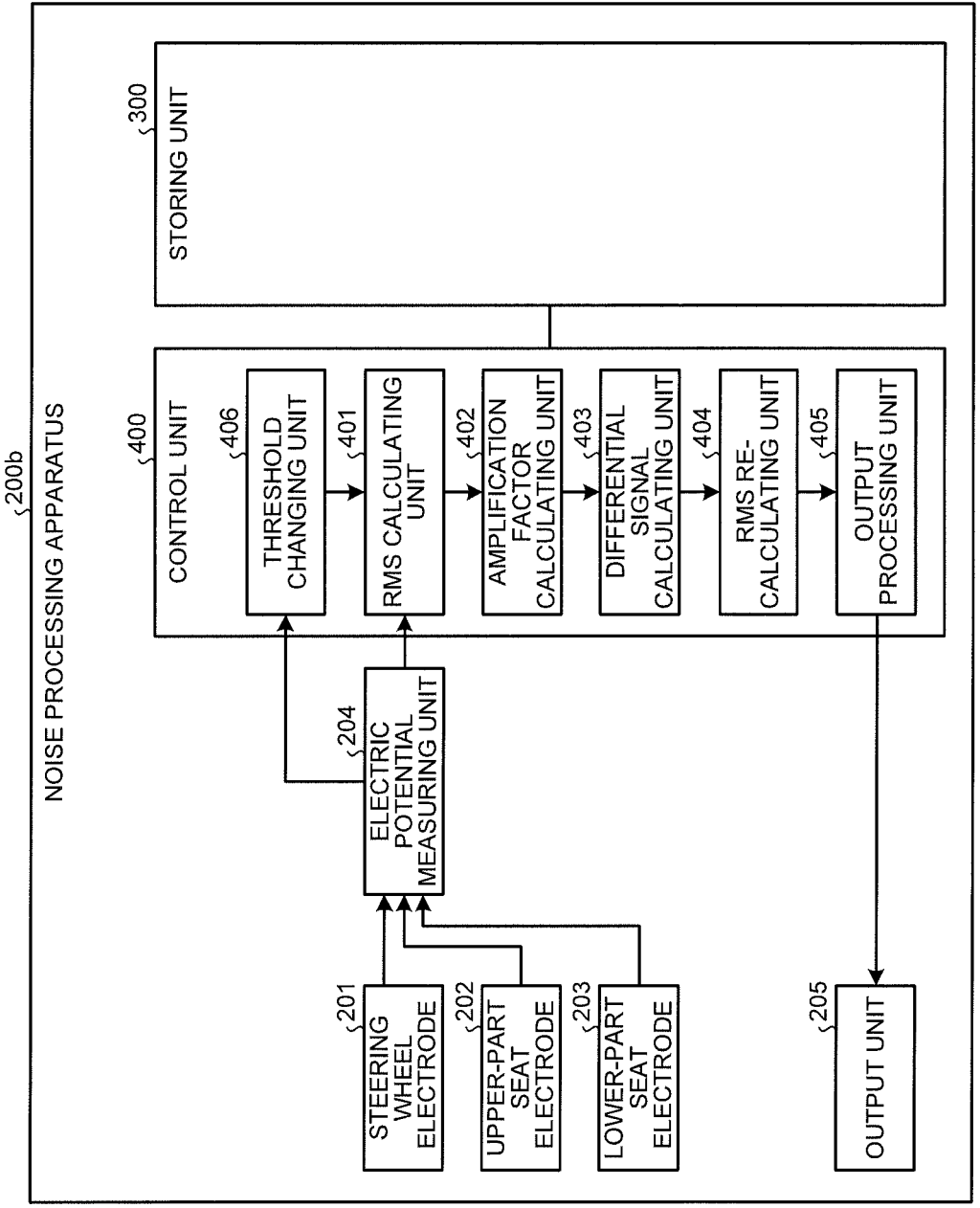
FIG. 21 is a block diagram illustrating an example configuration of a noise processing apparatus according to a fourth embodiment.

Configuration of the Noise Processing Apparatus According to the Fourth Embodiment An example configuration of the noise processing apparatus 200b according to the fourth embodiment will be described here with reference to FIG. 21. FIG. 21 is a block diagram illustrating an example configuration of a noise processing apparatus according to a fourth embodiment. As illustrated in FIG. 21, the noise processing apparatus 200b further includes a threshold changing unit 406 in addition to the units included in the noise processing apparatus 200 that has been described with reference to FIG. 2.

If the intensity of the first potential difference signal or the second potential difference signal is smaller than a threshold for a predetermined period, the RMS calculating unit 401 according to the fourth embodiment calculates the intensity by using an interval longer than that used in a case in which the intensity of the first potential difference signal or the second potential difference signal is not smaller than the threshold in a predetermined period. Furthermore, if the intensity of the first potential difference signal or the second potential difference signal is greater than the threshold, the RMS calculating unit 401 calculates the intensity by using an interval shorter than that used in a case in which the intensity of the first potential difference signal or the second potential difference signal is not greater than the threshold. The process performed by using the intensity calculating threshold in detail is the same as that in the third embodiment; therefore, a description thereof will be omitted. The RMS calculating unit 401 performs the process by using the intensity calculating threshold controlled by the threshold changing unit 406.

If the vehicle speed is higher than a predetermined threshold, the threshold changing unit 406 changes the intensity calculating threshold to a value greater than that used when the vehicle speed is lower than the predetermined threshold. Furthermore, if the vehicle speed is lower than the predetermined threshold, the threshold changing unit 406 changes the intensity calculating threshold to a value smaller than that used when the vehicle speed is higher than the predetermined threshold. In the following, as information indicating the vehicle speed, a case will be described of using three running states, i.e., "when a vehicle is idling", "when a vehicle is running on a general road", and "when a vehicle is running on an expressway". The vehicle speed increases in the order of "when a vehicle is idling", "when a vehicle is running on a general road", and "when a vehicle is running on an expressway". Specifically, the vehicle speed is the highest "when a vehicle is running on an expressway" from among the three states and the vehicle speed is the lowest "when a vehicle is idling".

Specifically, the threshold changing unit 406 determines the running state of the vehicle. For example, the threshold changing unit 406 acquires the vehicle speed from a memory control unit (MCU) in the vehicle or the current running position from the global positioning system (GPS).

More specifically, if the vehicle speed is, for example, 100 km or more, the threshold changing unit 406 determines that the vehicle is running at high speed. Furthermore, if the vehicle speed is, for example, 40 km or below, the threshold changing unit 406 determines that the vehicle is running at low speed. Furthermore, for example, if the vehicle speed is 0 km and the rotational speed of an engine is equal to or greater than a predetermined rotational speed, the threshold changing unit 406 determines that the vehicle is idling. In the above description, a case has been described in which, if the vehicle speed is 100 km or more, the threshold changing unit 406 determines that the vehicle is running at high speed; however, the present invention is not limited thereto. An arbitrary threshold may also be used. Furthermore, when determining whether the vehicle is idling or running on a general road, similarly, an arbitrary threshold may also be used.

Furthermore, for example, the threshold changing unit 406 determines the running state of the vehicle by using the waveform of the potential difference signal. For example, the threshold changing unit 406 previously stores the waveforms of the potential difference signals illustrated in FIGS. 19A to 19C by associating them with the running state of the vehicle. Specifically, the threshold changing unit 406 stores, in a memory, the waveforms of the potential difference signals illustrated in FIGS. 19A to 19C by associating them with the state of the vehicle, such as "the vehicle is idling", "the vehicle is running on a general road", and "the vehicle is running on an expressway". Then, the threshold changing unit 406 searches, the memory, for the waveform of the potential difference signal that matches the potential difference signal measured by the electric potential measuring unit 204 and acquires the running state associated with the waveform of the potential difference signal from the search result.

Furthermore, if the vehicle speed is higher than the predetermined threshold, the threshold changing unit 406 changes the intensity calculating threshold to a value greater than that used when the vehicle speed is lower than the predetermined threshold. Furthermore, if the vehicle speed is lower than the predetermined threshold, the threshold changing unit 406 changes the intensity calculating threshold to a value smaller than that used when the vehicle speed is higher than the predetermined threshold. In the following, a case will be described in which the intensity calculating threshold obtained when a vehicle is running on a general road is "200 mV".

If the vehicle is idling, the threshold changing unit 406 changes the intensity calculating threshold that is smaller than that used when the vehicle is running on a general road. For example, the threshold changing unit 406 changes the intensity calculating threshold to "100 mV" that is smaller than "200 mV". Furthermore, if the vehicle is running on a general road, the threshold changing unit 406 changes the intensity calculating threshold to "200 mV". Furthermore, if the vehicle is running on an expressway, the threshold changing unit 406 changes the intensity calculating threshold greater than that used when the vehicle is running on a general road. For example, the threshold changing unit 406 changes the intensity calculating threshold to "300 mV" that is greater than "200 mV".

In the above description, a case has been described in which the threshold changing unit 406 uses "100 mV", "200 mV", and "300 mV" as the intensity calculating threshold for the states of the vehicle, i.e., "when a vehicle is idling", "when a vehicle is running on a general road", and "when a vehicle is running on an expressway", respectively; however, the present invention is not limited thereto. An arbitrary value may also be used.

Furthermore, in the above description, a case has been described in which the threshold changing unit 406 uses three states of the vehicle, i.e., "idling", "running on a general road", and "running on an expressway"; however, the present invention is not limited thereto. For example, the threshold changing unit 406 may also use the actual running speed of the vehicle or arbitrary information. Furthermore, for example, in addition to the states of "idling", "running on a general road", and "running on an expressway", the threshold changing unit 406 may also use another running state and may also not use some state from among the states of "idling", "running on a general road", and "running on an expressway".

Figure 22:
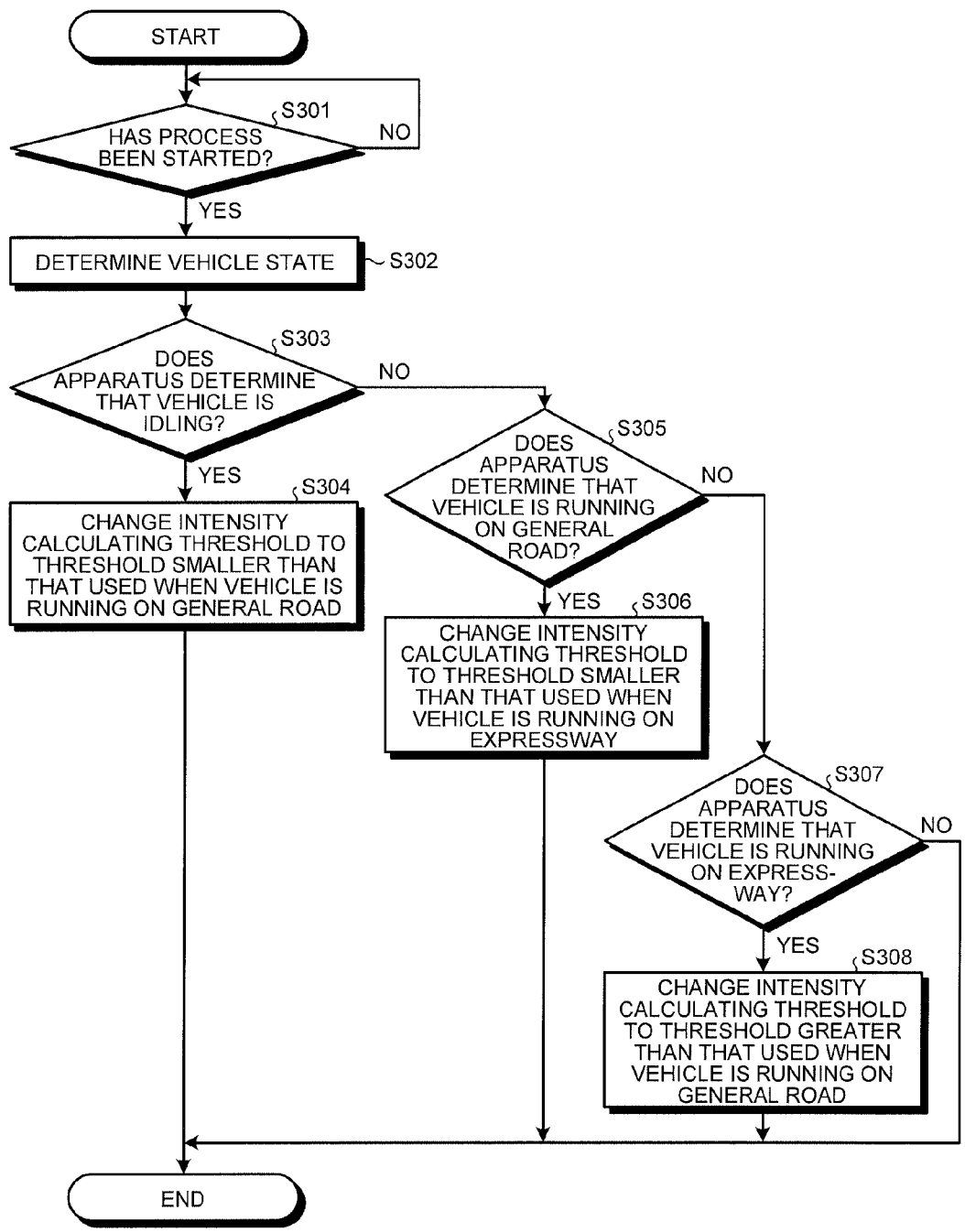
FIG. 22 is a flowchart illustrating an example of the flow of a process performed by a threshold changing unit according to the fourth embodiment.

Process Performed by the Threshold Changing Unit According to the Fourth Embodiment In the following, the flow of the process performed by the threshold changing unit 406 will be described with reference to FIG. 22. FIG. 22 is a flowchart illustrating an example of the flow of a process performed by a threshold changing unit according to the fourth embodiment. In FIG. 22, a description will be given of a case of using, as information indicating the vehicle speed, three running states, i.e., "idling", "running on a general road", and "running on an expressway".

As illustrated in FIG. 22, if the threshold changing unit 406 starts the process (Yes at Step S301), the threshold changing unit 406 determines the state of the vehicle (Step S302). Specifically, by using the vehicle speed or the waveform of the potential difference signal, the threshold changing unit 406 determines the state of the vehicle from among the states, i.e., "idling", "running on a general road", or "running on an expressway".

If the threshold changing unit 406 determines that the vehicle is idling (Yes at Step S303), the threshold changing unit 406 changes the intensity calculating threshold to a threshold smaller than that used when the vehicle is running on a general road (Step S304). For example, the threshold changing unit 406 changes the intensity calculating threshold to "100 mV" that is smaller than "200 mV". Furthermore, if the threshold changing unit 406 determines that the vehicle is running on a general road (No at Step S303 and Yes at Step S305), the threshold changing unit 406 changes the intensity calculating threshold to a threshold smaller than that used when the vehicle is running on an expressway (Step S306). For example, the threshold changing unit 406 changes the intensity calculating threshold to "200 mV" that is smaller than "300 mV". Furthermore, if the threshold changing unit 406 determines that the vehicle is running on an expressway (No at Step S303, No at Step S305, and Yes at Step S307), the threshold changing unit 406 changes the intensity calculating threshold to the threshold greater than that used when the vehicle is running on a general road (Step S308). For example, the threshold changing unit 406 changes the intensity calculating threshold to "300 mV" that is greater than "200 mV". Furthermore, if the threshold changing unit 406 determines that the state is neither of the states, i.e., "idling", "running on a general road", and "running on an expressway" (No at Step S303, No at Step S305, and No at Step S307), the threshold changing unit 406 does not change the intensity calculating threshold.

Advantage of the Fourth Embodiment

As described above, in the fourth embodiment, the noise processing apparatus 200b is arranged in a vehicle. Furthermore, if the intensity of the first potential difference signal or the second potential difference signal is smaller than the threshold for a predetermined period, the noise processing apparatus 200b calculates the intensity by using an interval longer than that used in a case in which the intensity is not small in a predetermined period. Furthermore, if the intensity of the first potential difference signal or the second potential difference signal is greater than the threshold, the noise processing apparatus 200b calculates the intensity by using an interval smaller than that used when the intensity is not greater than the threshold. Furthermore, if the vehicle speed is higher than the predetermined threshold, the noise processing apparatus 200b changes the intensity calculating threshold, used by the intensity calculating unit, to a value greater than that used in a case in which the vehicle speed is lower than the predetermined threshold. Furthermore, if the vehicle speed is lower than the predetermined threshold, the noise processing apparatus 200b changes the intensity calculating threshold to a value smaller than that used when the vehicle speed is higher than the predetermined threshold. Accordingly, the interval can be determined by using the intensity calculating threshold suitable for the running speed of the vehicle.

[e] Fifth Embodiment

Furthermore, for example, by using the difference calculated by using a potential difference signal that is acquired after acquiring a target potential difference signal to be corrected, the differential signal calculating unit 403 may also correct the first potential difference signal or the second potential difference signal obtained at the time of acquisition. Specifically, by using the difference between an interval between the starting point and the end point, the differential signal calculating unit 403 may also correct the first potential difference signal or the second potential difference signal obtained at the process time. Accordingly, in a fifth embodiment, a description will be given of a case in which, by using the difference calculated by using the potential difference signal that is acquired after the target potential difference signal is acquired, the first potential difference signal or the second potential difference signal is corrected.

Figure 23A:
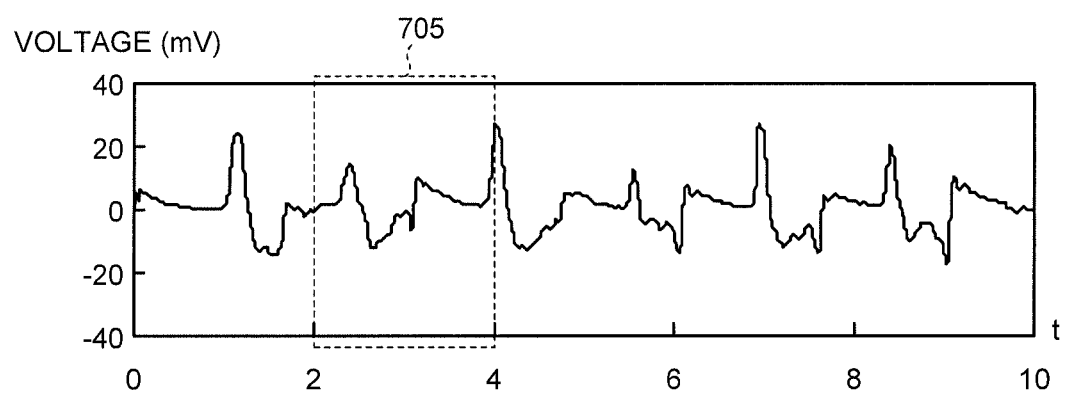
FIG. 23A is a schematic diagram illustrating a differential signal calculating unit according to a fifth embodiment.
Figure 23B:
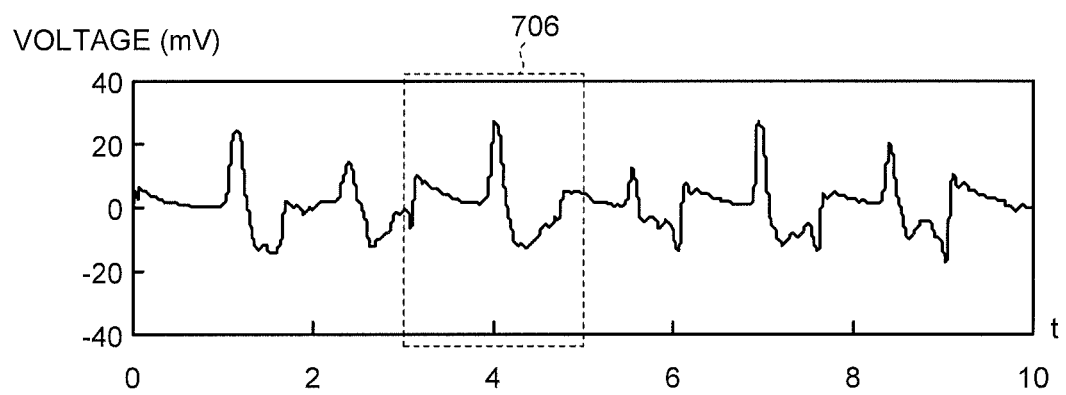
FIG. 23B is a schematic diagram illustrating the differential signal calculating unit according to the fifth embodiment.

In the following, the differential signal calculating unit 403 according to the fifth embodiment will be described with reference to FIGS. 23A and 23B. FIGS. 23A and 23B are schematic diagrams each illustrating a differential signal calculating unit according to a fifth embodiment. FIGS. 23A and 23B illustrate an example of the potential difference signal. In FIGS. 23A and 23B, the vertical axes indicate the value of the potential difference signal and the horizontal axes indicate the time axis. In the following, a case will be described in a case in which the interval is "2 seconds" and the potential difference signal obtained at 4 seconds is corrected.

Reference numerals 705 and 706 illustrated in FIGS. 23A and 23B denotes the range of the potential difference signals used by the RMS calculating unit 401. In this case, an interval, during which 4 seconds corresponding to the correction time is located between the starting point and the end point of the interval, corresponds to, for example, the interval during which 4 seconds is located between the starting point and the end point, as illustrated by reference numeral 706 in FIG. 23B. Furthermore, in the example illustrated in FIG. 23B, the starting point of the interval corresponds to 5 seconds and the end point of the interval corresponds to 3 seconds.

In the following, the purpose of using the difference calculated by using the potential difference signal that is acquired after the acquisition time will be briefly described. It is assumed that, when compared a case in which the difference related to the signals obtained 2 seconds before the correction starts is used with a case in which the difference related to the signals obtained for 2 seconds for which the correction is performed is used, the calculation result of the signal intensity differs depending on a change in noise. In the example illustrated in FIG. 23A, the peak is at 4 seconds. When correcting the peak located at 4 seconds, it is assumed that the difference related to the range including the entire peak located at 4 seconds accurately indicates the intensity difference at the peak located at 4 seconds when compared with the difference related to the range that does not include the entire peak located at 4 seconds. Accordingly, the differential signal calculating unit 403 corrects the potential difference signal by using the difference related to an interval during which the correction time is located between the starting and end points.

A noise processing apparatus 200c according to the fifth embodiment will be described here. In the following, a description will be given of a case in which the RMS calculating unit 401 calculates the intensity of the potential difference signal in real time by using the potential difference signal during the 2 seconds before the process time begins. In the following, a description will be given of a case in which the RMS calculating unit 401 performs the calculation in real time; however, the present invention is not limited thereto. For example, the RMS calculating unit 401 may also perform the calculation at one-second intervals by using "2 seconds" as the interval. Specifically, the RMS calculating unit 401 may also calculate, at one-second intervals, the potential difference signal obtained from the process time to 2 seconds before the calculation. In a case of the second embodiment, the differential signal calculating unit 403 corrects the potential difference signal obtained at 4 seconds by using the difference related to the potential difference signals between 2 seconds and 4 seconds.

At this time, as illustrated by reference numeral 705 in FIG. 23A, the amplification factor calculating unit 402 calculates, at 4 seconds, the difference between the potential difference signals obtained between 2 seconds and 4 seconds. Furthermore, as illustrated by reference numeral 706 in FIG. 23B, the amplification factor calculating unit 402 calculates, at 5 seconds, the difference between the potential difference signals obtained between 3 seconds and 5 seconds.

The differential signal calculating unit 403 corrects the first potential difference signal or the second potential difference signal at the time of acquisition by using the difference calculated using a potential difference signal that is acquired after the acquisition. For example, the differential signal calculating unit 403 corrects, at 5 seconds, the potential difference signal obtained between 4 seconds by using the difference between the potential difference signals obtained between 3 seconds and 5 seconds. Specifically, the potential difference signal is corrected by using the difference related to the interval during which a point of 4 seconds is located between the starting and end points. In such a case, because the potential difference signal obtained at 4 seconds is corrected by using the difference calculated at 5 seconds, the output processing unit 405 outputs the potential difference signal with a time lag of 1 second.

As described above, according to the fifth embodiment, because the differential signal calculating unit 403 performs the correction by using the difference related to an interval in which the acquisition time is located between the starting and end points, noise can be appropriately reduced.

[f] Sixth Embodiment

Figure 24:
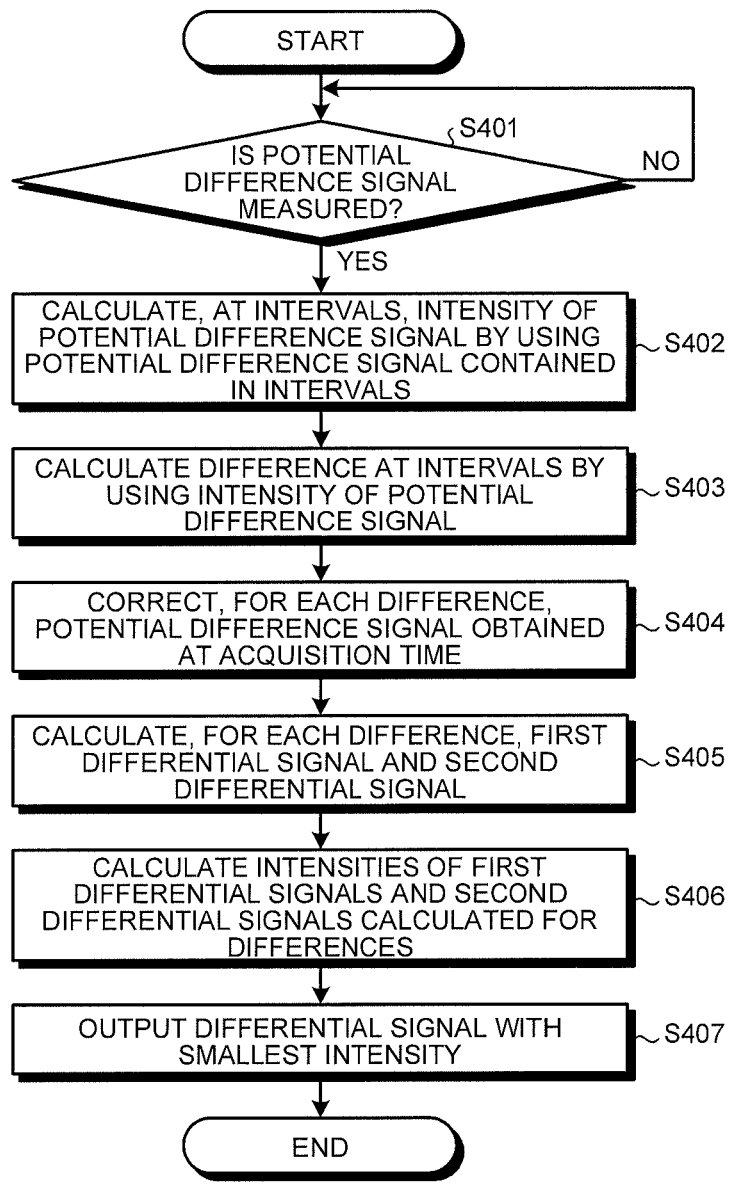
FIG. 24 is a flowchart illustrating an example of the flow of a process performed by a noise processing apparatus according to the fifth embodiment.

A noise processing apparatus 200d may also calculate differential signals at multiple intervals including the acquisition time of the potential difference signal to be corrected and output a differential signal that contains the lowest noise. Accordingly, in a sixth embodiment, a case will be described with reference to FIG. 24, in which the noise processing apparatus 200d calculates differential signals at multiple intervals and outputs a differential signal containing the lowest noise. FIG. 24 is a flowchart illustrating an example of the flow of a process performed by the noise processing apparatus 200d according to the fifth embodiment. In the following, a description will be given of a case in which the correction is performed on the potential difference signal obtained at 4 seconds.

As illustrated in FIG. 24, in the sixth embodiment, if the potential difference signal is measured (Yes at Step S401), the RMS calculating unit 401 calculates, at multiple intervals containing the acquisition time of the potential difference signal to be corrected, the intensities of the potential difference signals by using the potential difference signals contained in the intervals (Step S402). For example, the RMS calculating unit 401 calculates the intensities of the potential difference signals at multiple different intervals, such as from 2 seconds to 4 seconds, from 3 seconds to 5 seconds, from 4 seconds to 6 seconds, from 2 seconds to 5 seconds, and from 3 seconds to 6 seconds. Furthermore, the RMS calculating unit 401 may also use different intervals or may not use the different intervals.

Then, the amplification factor calculating unit 402 calculates the differences at multiple intervals containing the acquisition time of the potential difference signal to be corrected by using the intensities of the potential difference signals calculated by the RMS calculating unit 401 (Step S403). For example, for the intervals, such as from 2 seconds to 4 seconds, from 3 seconds to 5 seconds, from 4 seconds to 6 seconds, from 2 seconds to 5 seconds, and from 3 seconds to 6 seconds, the amplification factor calculating unit 402 calculates the differences of "1.49", "1.3", "1.9", "1.4", and "1.8".

Then, for the differences calculated by the amplification factor calculating unit 402, the differential signal calculating unit 403 corrects the potential difference signals obtained at the acquisition time of the potential difference signal to be corrected (Step S404). For example, for the differences of "1.49", "1.3", "1.9", "1.4", and "1.8", the differential signal calculating unit 403 corrects the potential difference signals. Specifically, for the potential difference signal obtained at 4 seconds, the differential signal calculating unit 403 corrects the potential difference signal by using the difference of "1.49" and corrects the potential difference signal by using the difference of "1.3". Furthermore, the differential signal calculating unit 403 also corrects the potential difference signal for the differences of "1.9", "1.4", and "1.8".

Then, for the corrected potential difference signals obtained after the acquisition of the potential difference signals to be corrected, the differential signal calculating unit 403 calculates, for the differences, the first differential signals and the second differential signals (Step S405). For example, for the potential difference signal obtained at 4 seconds, the differential signal calculating unit 403 calculates the first differential signal and the second differential signal by using the potential difference signal corrected using the difference of "1.49". Furthermore, similarly, for the differences of "1.3", "1.9", "1.4", and "1.8", the differential signal calculating unit 403 also calculates the first differential signals and the second differential signals.

Then, for each of the first differential signals and the second differential signals calculated by the differential signal calculating unit 403 for each difference, the RMS re-calculating unit 404 calculates each of the intensities of the differential signals (Step S406). For example, for the first differential signal and the second differential signal associated with the difference of "1.49", the RMS re-calculating unit 404 calculates each of the intensities of the differential signals. Furthermore, similarly, for the differences of "1.3", "1.9", "1.4", and "1.8", the RMS re-calculating unit 404 calculates each of the intensities of the first differential signals and the second differential signals.

Then, from among the first differential signals and the second differential signals calculated for the differences, the output processing unit 405 outputs a differential signal having the smallest intensity (Step S407). Specifically, from among the intensities calculated by the RMS re-calculating unit 404, the output processing unit 405 specifies the smallest intensity and outputs the differential signal associated with the specified intensity.

As described above, according to the sixth embodiment, the noise processing apparatus 200d calculates the differences at multiple intervals that contains the correction time and uses the best difference for the noise reduction from among the calculated differences; therefore, it is possible to precisely reduce the noise.

[g] Seventh Embodiment

In the above explanation, a description has been given of the embodiments according to the present invention; however, the embodiments are not limited thereto and can be implemented with various kinds of embodiments other than the embodiments described above. Therefore, another embodiment will be described below.

Output Processing Unit

For example, in the embodiments described above, a description has been given of a case in which the output processing unit 405 simply selects the potential difference signal with the smaller intensity; however, the present invention is not limited thereto. For example, the output processing unit 405 may also calculate each of the ratios of the heartbeat signal to each of the two potential difference signals and may outputs the calculated potential difference signal having the larger heart beat ratio.

System Configuration

Furthermore, of the processes described in the embodiments, the whole or a part of the processes that are mentioned as being automatically performed can be manually performed or the whole or a part of the processes that are mentioned as being manually performed can be automatically performed using known methods. For example, in the example illustrated in FIG. 22, a subject may also input the state of the vehicle. In such a case, the noise processing apparatus performs the process by using the state of the vehicle that is input by the subject. Furthermore, the flow of the processes, the control procedures, the specific names, and the information (FIGS. 1 to 24) containing various kinds of data or parameters indicated in the above specification and drawings can be arbitrarily changed unless otherwise noted.

The components of each unit illustrated in the drawings are only for conceptually illustrating the functions thereof and are not necessarily physically configured as illustrated in the drawings. In other words, the specific shape of a separate or integrated unit is not limited to the drawings; however, all or part of the unit can be configured by functionally or physically separating or integrating any of the units depending on various loads or use conditions. For example, in the example illustrated in FIG. 2, the steering wheel electrode 201 or the upper-part seat electrode 202 may also be used as an external unit of the noise processing apparatus and be connected via a network, such as a wireless local area network (LAN), such that they cooperate with each other.

Computer

Figure 25:
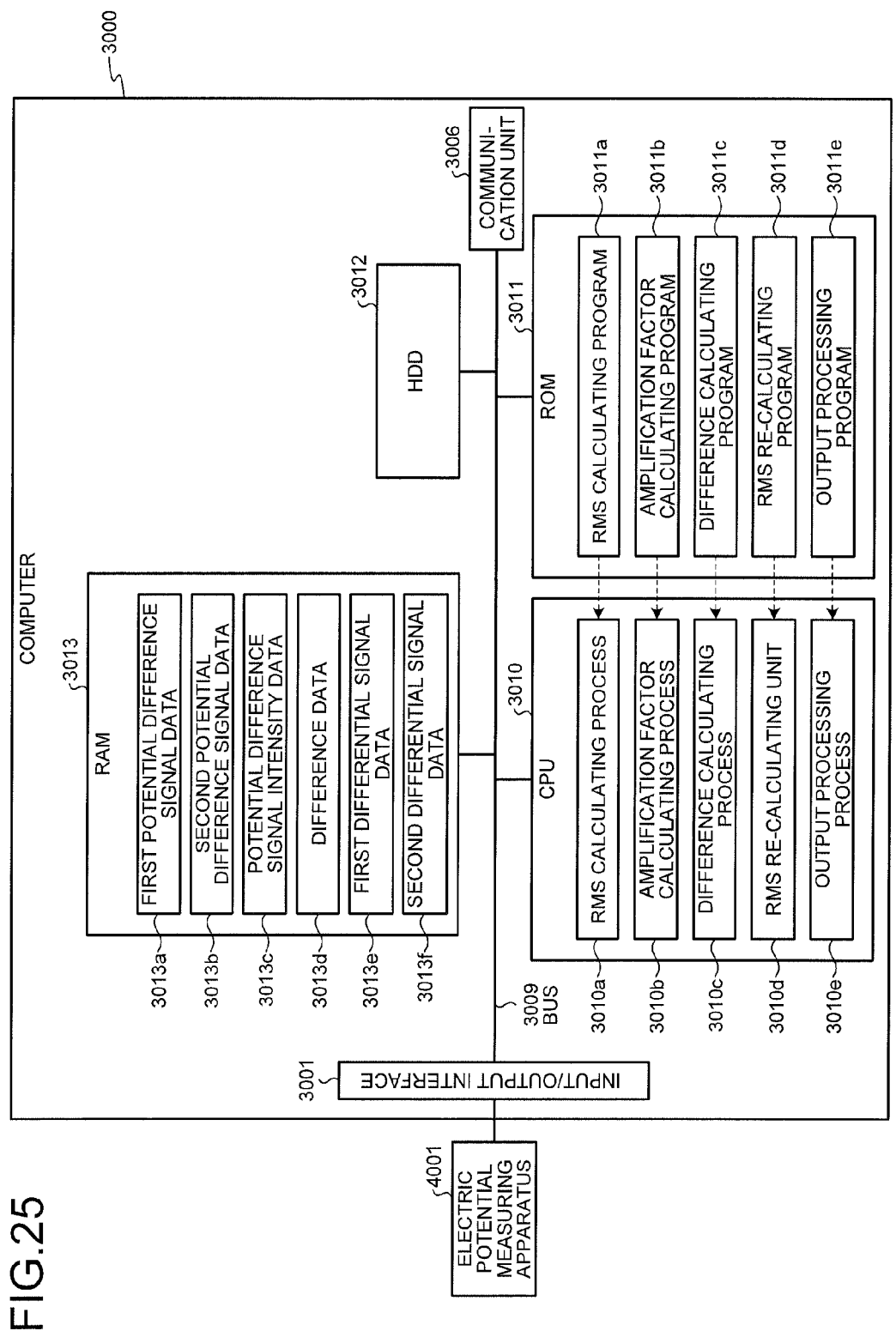
FIG. 25 is a block diagram illustrating an example of a computer that executes a noise processing program according to the second embodiment.

The various processes described in the above embodiments can be implemented by programs prepared in advance and executed by a computer such as a personal computer or a workstation. Accordingly, in the following, a computer that executes a noise processing program having the same function performed by the apparatus in the above embodiments will be described, as an example, with reference to FIG. 25. FIG. 25 is a block diagram illustrating an example of a computer that executes a noise processing program according to the second embodiment.

As illustrated in FIGS. 20A to 20C, a computer 3000 according to the second embodiment includes an input/output interface 3001, a communication unit 3006, a CPU 3010, and a ROM 3011. Furthermore, the computer 3000 also includes a hard disk drive (HDD) 3012 and a random access memory (RAM) 3013. Each of the units included in the computer 3000 is connected via a bus 3009. Furthermore, the computer 3000 is connected to an electric potential measuring apparatus 4001 via the input/output interface 3001. The electric potential measuring apparatus 4001 corresponds to the electric potential measuring unit 204.

The ROM 3011 stores therein, in advance, a control program exhibiting the same function as the RMS calculating unit 401, the amplification factor calculating unit 402, the differential signal calculating unit 403, the RMS re-calculating unit 404, and the output processing unit 405 described in the second embodiment. Specifically, as illustrated in FIG. 25, the ROM 3011 stores therein, in advance, an RMS calculating program 3011a, an amplification factor calculating program 3011b, a difference calculating program 3011c, an RMS re-calculating program 3011d, and an output processing program 3011e. These programs 3011a to 3011e may also be integrated or separated in the same manner as the components of the noise processing apparatus 200 illustrated in FIG. 2.

The CPU 3010 reads these programs 3011a to 3011e from the ROM 3011 and executes them. Accordingly, as illustrated in FIG. 25, the programs 3011a to 3011c function as an RMS calculating process 3010a, an amplification factor calculating process 3010b, and a difference calculating process 3010c, respectively. Furthermore, the programs 3011d to 3011e function as an RMS re-calculating unit 3010d and an output processing process 3010e, respectively. The processes 3010a to 3010e correspond to the RMS calculating unit 401, the amplification factor calculating unit 402, the differential signal calculating unit 403, the RMS re-calculating unit 404, and the output processing unit 405, respectively, illustrated in FIG. 2.

Then, the CPU 3010 executes the noise processing program by using data stored in the RAM 3013. For example, the CPU 3010 uses first potential difference signal data 3013a, second potential difference signal data 3013b, potential difference signal intensity data 3013c of a potential difference signal, difference data 3013d, and first differential signal data 3013e. Furthermore, the CPU 3010 uses second differential signal data 3013f.

Additional

The noise processing program described in the embodiments can be distributed via a network, such as the Internet. Furthermore, the noise processing program may also be stored in a computer-readable recording medium, such as a hard disk, a flexible disk (FD), a CD-ROM, an MO, and a DVD and be implemented by the computer reading it from the recording medium.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A noise processing apparatus comprising:
a first measuring unit that measures a first potential difference signal between a first electrode that is arranged at a location other than a steering unit in an apparatus and a second electrode that is used as a reference electrode;
a second measuring unit that measures a second potential difference signal between the second electrode and a third electrode that is arranged on the steering unit in the apparatus;
an intensity calculating unit that calculates a predetermined period of the first potential difference signal and second values each corresponding to a predetermined period of the second potential difference signal;
a difference calculating unit that calculates differences between the first values and the second values, respectively;
a correction unit that corrects, at the each predetermined period of the first potential difference signal and the second potential difference signal by equalizing the differences between the first values and the second values using each corresponding difference calculated by the difference calculating unit;
a differential signal calculating unit that calculates, a differential signal indicating a difference between the first potential difference signal and the second potential difference signal, the first potential difference signal used by the differential signal calculating unit being a corrected first potential difference signal when the first potential difference signal is corrected, and the second potential difference signal used by the differential signal calculating unit being a corrected second potential difference signal when the second potential difference signal is corrected; and
an output processing unit that outputs the differential signal calculated by the differential signal calculating unit.

2. The noise processing apparatus according to claim 1, wherein
the differential signal calculating unit calculates a first differential signal by performing a subtraction process for subtracting the second potential difference signal from the first potential difference signal or by performing a subtraction process for subtracting the first potential difference signal from the second potential difference signal, and calculates a second differential signal by performing an addition process for adding the first potential difference signal to the second potential difference signal, and
the output processing unit calculates a first value of the first differential signal and a second value of the second differential signal, which are calculated by the differential signal calculating unit, and outputs whichever of the differential signals has a lower calculated value than the other differential signal.

3. The noise processing apparatus according to claim 2, wherein the intensity calculating unit calculates the first values and the second values in accordance with the state of the first potential difference signal and/or the second potential difference signal.

4. The noise processing apparatus according to claim 3, wherein
the noise processing apparatus is arranged in a vehicle,
when the first values and/or the second values for a predetermined period are lower than a threshold, the intensity calculating unit calculates first values and/or second values by using the predetermined period that is longer than that used in a case in which the first values and/or the second values are not lower than the threshold, whereas, when the first values and/or the second values for a predetermined period are greater than the threshold, the intensity calculating unit calculates first values and/or second values by using the predetermined period that is shorter than that used in a case in which the first values and/or the second values are not greater than the threshold, and
further comprising a threshold changing unit that changes, when the speed of the vehicle is higher than a predetermined threshold, an intensity calculating threshold, which is a threshold used by the intensity calculating unit, to a value greater than a value used when the speed of the vehicle is lower than the predetermined threshold and that changes, when the speed of the vehicle is lower than the predetermined threshold, the intensity calculating threshold to a value smaller than a value used when the speed of the vehicle is higher than the predetermined threshold.

5. The noise processing apparatus according to claim 4, wherein, by using a difference calculated by using a potential difference signal that is acquired after an acquisition time of a potential difference signal that is to be corrected, the correction unit corrects the first potential difference signal and/or the second potential difference signal obtained at a correction time.

6. The noise processing apparatus according to claim 5, wherein
the intensity calculating unit calculates, at multiple predetermined periods containing the acquisition time, intensities of potential difference signals by using the potential difference signals included in the predetermined periods,
the difference calculating unit calculates the differences for each at multiple predetermined periods containing the acquisition time,
the correction unit corrects, for each difference calculated by the difference calculating unit, the potential difference signals obtained at the acquisition time,
the differential signal calculating unit calculates, for each difference, first differential signals and second differential signals by using the potential difference signals that are obtained at the acquisition time, that are calculated by the difference calculating unit, and that are corrected for the differences, and
from among the first differential signals and the second differential signals calculated by the differential signal calculating unit, the output processing unit outputs a differential signal having the lowest intensity.

7. The noise processing apparatus according to claim 1, wherein the calculating of the first values and the second values includes calculating the first values and the second values by calculating RMS (Root Mean Square) values each corresponding to the each predetermined period of the first potential difference signal and the second potential difference signal, respectively.

8. A non-transitory computer readable storage medium having stored therein a noise processing program causing a computer to execute a process comprising:
measuring a first potential difference signal between a first electrode that is arranged at a location other than a steering unit in an apparatus and a second electrode that is used as a reference electrode;
measuring a second potential difference signal between the second electrode and a third electrode that is arranged on the steering unit in the apparatus;

calculating first values each corresponding to a predetermined period of the first potential difference signal measured at the measuring the first potential difference signal and second values each corresponding to a predetermined period of the second potential difference signal calculated at the measuring the second potential difference signal;

calculating differences between the first values and the second values, respectively;

correcting at the each predetermined period of the first potential difference signal and/or the second potential difference signal by equalizing the differences between the first values and the second values using each corresponding difference calculated at the calculating the difference;

calculating a differential signal indicating a difference between the first potential difference signal and the second potential difference signal, the first potential difference signal used in calculating the differential signal being a corrected first potential difference signal when the first potential difference signal is corrected, and the second potential difference signal used in calculating the differential signal being a corrected second potential difference signal when the second potential difference signal is corrected; and outputting the differential signal calculated at the calculating the differential signal.

9. The non-transitory computer readable storage medium according to claim 8, wherein the calculating the differential signal includes calculating a first differential signal by performing a subtraction process for subtracting the second potential difference signal from the first potential difference signal or by performing a subtraction process for subtracting the first potential difference signal from the second potential difference signal, and includes calculating a second differential signal by performing an addition process for adding the first potential difference signal to the second potential difference signal, and the outputting includes calculating a first value of the first differential signal and a second value of the second differential signal, which are calculated at the calculating the differential signal, and includes outputting whichever of the differential signals has a lower calculated value than the other differential signal.

10. The non-transitory computer readable storage medium according to claim 9, wherein the calculating the intensity includes calculating the first values and the second values in accordance with the state of the first potential difference signal and/or the second potential difference signal.

11. The non-transitory computer readable storage medium according to claim 10, wherein when a waveform of the first potential difference signal and/or the second potential difference signal varies lower than a threshold, the calculating the intensity includes calculating the first values or second values by using a predetermined period that is longer than an interval used in a case in which the waveform of the first potential difference signal and/or the second potential difference signal does not vary lower than the threshold for a predetermined period, when the waveform of the first potential difference signal and/or the second potential difference signal varies greater than the threshold, the calculating the intensity includes calculating the first values or second values by using the predetermined period that is shorter than an interval used in a case in which the waveform of the first potential difference signal and/or the second potential difference signal does not vary greater than the threshold, and further comprising changing, when the speed of a vehicle is higher than a predetermined threshold, an intensity calculating threshold, which is a threshold used at the calculating the intensity, to a value greater than a value used when the speed of the vehicle is lower than the predetermined threshold, and changing, when the speed of the vehicle is lower than the predetermined threshold, the intensity calculating threshold to a value smaller than a value used when the speed of the vehicle is higher than the predetermined threshold.

12. The non-transitory computer readable storage medium according to claim 11, wherein, by using a difference calculated using a potential difference signal that is acquired after an acquisition time of a potential difference signal that is to be corrected, the correcting includes correcting the first potential difference signal and/or the second potential difference signal obtained at a correction time.

13. The non-transitory computer readable storage medium according to claim 12, wherein the calculating the intensity includes calculating, at multiple predetermined periods containing the acquisition time, intensities of potential difference signals by using the potential difference signals included in the predetermined periods, the calculating the difference includes calculating the differences, for each multiple predetermined periods containing the acquisition time, the correcting includes correcting, for each difference calculated at the calculating the difference, the potential difference signals obtained at the acquisition time, the calculating the differential signal includes calculating, for each difference, first differential signals and second differential signals by using the potential difference signals that are obtained at the acquisition time, that are calculated at the calculating the difference, and that are corrected for the differences, and from among the first differential signals and the second differential signals calculated at the calculating the differential signal, the outputting includes outputting a differential signal having the lowest intensity.

14. The non-transitory computer readable storage medium according to claim 8, wherein the calculating of the first values and the second values includes calculating the first values and the second values by calculating RMS (Root Mean Square) values each corresponding to the each predetermined period of the first potential difference signal and the second potential difference signal, respectively.

15. A noise processing apparatus comprising:
a memory; and
a processor coupled to the memory, wherein the processor executes a process comprising:
measuring a first potential difference signal between a first electrode that is arranged at a location other than a steering unit in an apparatus and a second electrode that is used as a reference electrode;
measuring a second potential difference signal between the second electrode and a third electrode that is arranged on the steering unit in the apparatus;
calculating, at predetermined intervals, an intensity of the first potential difference signal measured at the measuring the first potential difference signal and an intensity of the second potential difference signal calculated at the measuring the second potential difference signal;
calculating, at the predetermined intervals, a difference between the intensity of the first potential difference signal and the intensity of the second potential difference signal, which are calculated at the calculating the intensity;

correcting, at the predetermined intervals, the first potential difference signal and/or the second potential difference signal by using the difference calculated at the calculating the difference such that the intensity of the first potential difference signal and the intensity of the second potential difference signal are canceled out;

calculating a differential signal indicating a difference between the first potential difference signal and the second potential difference signal by using the potential difference signal corrected at the correcting at the predetermined intervals; and outputting the differential signal calculated at the calculating the differential signal.

* * * * *

UNITED STATES PATENT AND TRADEMARK OFFICE
CERTIFICATE OF CORRECTION

PATENT NO. : 9,000,931 B2
APPLICATION NO. : 13/483350
DATED : April 7, 2015
INVENTOR(S) : Hideki Tomimori et al.

It is certified that error appears in the above-identified patent and that said Letters Patent is hereby corrected as shown below:

Claims

Claim 1, Column 33, Line 11

After "calculates" insert --first values each corresponding to--.

Signed and Sealed this
Twentieth Day of October, 2015

Michelle K. Lee
*Director of the United States Patent and Trademark Office*